(12) United States Patent  (10) Patent No.: US 8,198,058 B2
Offerman  (45) Date of Patent: Jun. 12, 2012

(54) EFFICIENT USE OF BIOGAS CARBON DIOXIDE IN LIQUID FUEL SYNTHESIS

(76) Inventor: John D. Offerman, Orono, MN (US)

( * ) Notice: Subject to any disclaimer, the term of this patent is extended or adjusted under 35 U.S.C. 154(b) by 1049 days.

(21) Appl. No.: 12/074,749

(22) Filed: Mar. 5, 2008

(65) Prior Publication Data

US 2008/0220489 A1   Sep. 11, 2008

Related U.S. Application Data

(60) Provisional application No. 60/904,981, filed on Mar. 5, 2007.

(51) Int. Cl.
*C12P 7/08* (2006.01)
*C12P 7/06* (2006.01)
(52) U.S. Cl. ........................ 435/163; 435/161
(58) Field of Classification Search .................. 435/157, 435/289.1
See application file for complete search history.

(56) References Cited

U.S. PATENT DOCUMENTS

| | | | |
|---|---|---|---|
| 3,740,204 A * | 6/1973 | Slater et al. ...................... | 48/215 |
| 3,859,230 A * | 1/1975 | Moe .............................. | 252/373 |
| 4,235,801 A | 11/1980 | Bhasin | |
| 4,333,852 A | 6/1982 | Warren | |
| 4,339,546 A * | 7/1982 | Randalls ........................ | 518/704 |
| 4,492,772 A | 1/1985 | Ball | |
| 4,571,384 A | 2/1986 | Morita | |
| 4,650,814 A * | 3/1987 | Keller ............................ | 518/703 |
| 4,675,344 A | 6/1987 | Conway | |
| 4,749,724 A | 6/1988 | Quarderer | |
| 4,752,622 A | 6/1988 | Stevens | |
| 4,752,623 A | 6/1988 | Stevens | |
| 4,758,600 A | 7/1988 | Arimitsu | |
| 4,762,858 A | 8/1988 | Hucul | |
| 5,079,267 A * | 1/1992 | Kao et al. ...................... | 518/704 |

(Continued)

FOREIGN PATENT DOCUMENTS

EP   0 235 886 A2   9/1987

(Continued)

OTHER PUBLICATIONS

Jens R. Rostrup-Nielsen and Jens Sehested and Jens K. Nørskov. "Hydrogen and synthesis gas by steam- and C02 reforming." Advances in Catalysis 47 (2002), pp. 65-139.*

(Continued)

*Primary Examiner* — Chris R Tate
*Assistant Examiner* — Douglas F White
(74) *Attorney, Agent, or Firm* — Hugh McTavish (57) ABSTRACT

The invention provides methods for producing methanol, higher alcohols (containing 2 or more carbons), in particular ethanol, or diesel fuel from biological wastes such as manure, sewage, and crop wastes, as well as from other organic materials. In the methods, organic material is first fermented by anaerobic microorganisms to a biogas consisting primarily of methane and carbon dioxide. The biogas is then converted to synthesis gas consisting primarily of CO and $H_2$. The synthesis gas is then contacted with a liquid fuel production catalyst to synthesize higher alcohols or other liquid fuels. The invention involves converting $CO_2$ in the biogas to synthesis gas by combining a $CO_2$ reforming reaction with steam reforming or partial oxidation to convert the biogas to synthesis gas. The invention also provides methods involving recirculating $CO_2$ from the output of the liquid fuel production reaction to one or more of the fermentation reaction, the $CO_2$ reforming reaction, or the liquid fuel production reaction.

24 Claims, 6 Drawing Sheets

U.S. PATENT DOCUMENTS

| | | | |
|---|---|---|---|
| 5,185,079 | A | 2/1993 | Dague |
| 5,500,449 | A * | 3/1996 | Benham et al. ............... 518/700 |
| 5,543,049 | A | 8/1996 | Hogen |
| 5,620,893 | A | 4/1997 | Hogen |
| 5,667,673 | A | 9/1997 | Hogen |
| 5,753,143 | A * | 5/1998 | Bhat et al. ..................... 252/373 |
| 5,821,111 | A * | 10/1998 | Grady et al. ............... 435/252.5 |
| 6,090,312 | A * | 7/2000 | Ziaka et al. ................... 252/373 |
| 6,248,796 | B1 | 6/2001 | Jackson |
| 6,254,807 | B1 * | 7/2001 | Schmidt et al. ............... 252/373 |
| 6,548,447 | B1 * | 4/2003 | Yokoyama et al. ........... 502/331 |
| 6,565,824 | B1 * | 5/2003 | Lightner .................... 423/418.2 |
| 6,601,543 | B2 | 8/2003 | Rautenbach |
| 6,802,974 | B2 | 10/2004 | Rebholz |
| 6,824,682 | B2 * | 11/2004 | Branson ........................ 210/603 |
| 6,872,378 | B2 * | 3/2005 | Weimer et al. ................ 423/650 |
| 7,160,342 | B2 * | 1/2007 | Grieve et al. ................ 48/198.1 |
| 7,169,821 | B2 * | 1/2007 | Branson ........................ 518/702 |
| 7,309,592 | B2 * | 12/2007 | Offerman et al. ............. 435/161 |
| 2005/0210739 | A1 * | 9/2005 | Esen et al. ...................... 44/605 |
| 2005/0266540 | A1 | 12/2005 | Offerman |
| 2006/0165582 | A1 * | 7/2006 | Brooker et al. ............... 423/414 |
| 2007/0010588 | A1 * | 1/2007 | Pearson ........................ 518/701 |
| 2007/0083073 | A1 * | 4/2007 | Bagherzadeh et al. ....... 585/943 |
| 2007/0298478 | A1 | 12/2007 | Offerman |
| 2009/0081746 | A1 * | 3/2009 | Liao et al. ..................... 435/160 |

FOREIGN PATENT DOCUMENTS

| | | |
|---|---|---|
| EP | 0253 540 A1 | 1/1988 |
| WO | WO 03/042117 A1 | 5/2003 |
| WO | WO 2005118826 A1 * | 12/2005 |

OTHER PUBLICATIONS

Bao, J. et al., 2003, A highly active K-Co-Mo/C catalyst for mixed alcohol synthesis from CO and H2. Chem. Commun. 2003:746-747.

Beretta, A. et al., 1996, Production of methanol and isobutyl alcohol mixtures over double-bed cesium-promoted Cu/ZnO/Cr2O3 and ZnO/Cr2O3 catalysts. Ind. Eng. Chem. Res. 35:1534-1542.

Beretta, A. et al., 1998, Development of a process for higher alcohol production via synthesis gas. Ind. Eng. Chem. Res. 37:3896-3908.

Bian, G.-Z. et al., 1998, Mixed alcohol synthesis from syngas on sulfide K-Mo-based catalysts: influence of support acidity. Ind. Eng. Chem. Res. 37:1736-1743.

Bredwell, M.D. et al., 1999, Reactor design issues for synthesis gas fermentations. Biotechnol. Prog. 15:834-844.

Breman, B.B. et al., 1995, Kinetics of the gas-slurry methanol-higher alcohol synthesis from CO/CO2/H2 over a Cs-Cu/ZnO/A12O3 catalyst, including simultaneous formation of methyl esters and hydrocarbons. Catalysis Today 24:5-14.

Burcham, M.M. et al., 1998, Higher alcohol synthesis over double bed Cs-Cu/ZnO/Cr2O3 catalysts: optimizing the yields of 2-methyl-1-propanol (isobutanol). Ind. Eng. Chem. Res. 37:4657-4668.

Ehwald, H. et al., 1991, A bicomponent catalyst for the selective formation of ethanol from synthesis gas. Applied Catalysis 76: 153-169.

Iranmahboob, J. et al., 2003, Dispersion of alkali on the surface of Co-MoS2/clay catalyst: a comparison of K and Cs as a promoter for synthesis of alcohol. Applied Catalysis A: General 247:207-218.

Klasson, K.T. et al., 1992, Biological conversion of synthesis gas into fuels. Int. J. Hydrogen Energy 17:281-288.

Klasson, K.T. et al., 1993, Biological conversion of coal and coal-derived synthesis gas. Fuel 72:1673-1678.

Matsuzaki, T. et al., 1993, Effect of transtion metals on oxygenates formation from syngas over Co/SiO2. Applied Catalysis A: General 105: 159-184.

Pereira, E.B. et al., 1993, Alcohol synthesis from syngas over nickel catalysts: effect of copper and lithium addition. Applied Catalysis A: General 103:291-309.

Smith, K.J., C.-W. Young, R.G. Herman, and K. Klier, 1991, Development of a kinetic model for alcohol synthesis over a cesium-promoted Cu/ZnO catalyst. Ind. Eng. Chem. Res. 30:61-71.

Stiles, A.B. et al., 1991, Catalytic conversion of synthesis gas to methanol and other oxygenated products. Ind. Eng. Chem. Res. 30:811-821.

Sun, X and G.W. Roberts, 2003, Synthesis of higher alcohols in a slurry reactor with cesium-promoted zinc chromite catalyst in decahydronaphthalene. Applied Catalysis A: General 247:133-142.

Suvajittanont, W. et al., 2003, Potential of biogas recirculation to enhance biomass accumulation on supporting media. Bioreseource Technology 88:157-162.

Worden, R.M. et al., 1991, Production of butanol and ethanol from synthesis gas via fermentation. Fuel 70: 615-619.

Barik, S. et al. 1988, Biological conversion of coal gas to methane. Appl. Biochem. and Biotech. 18:379-392.

Vega, J.L., et al., The biological production of ethanol from synthesis gas. Appl. Biochem. Biotechnol. 20/21:781-797, 1989.

* cited by examiner

EFFICIENT USE OF BIOGAS CARBON DIOXIDE IN LIQUID FUEL SYNTHESIS

This application claims priority under 35 U.S.C. §119(e) from U.S. provisional patent application Ser. No. 60/904,981, filed Mar. 5, 2007.

BACKGROUND

Disposal of municipal sewage and agricultural waste is often a costly process. Sewage and biological wastes, such as manure, are often disposed of by anaerobic microbial digestion to convert the digestible solid and liquid matter to a biogas composed primarily of $CH_4$ and $CO_2$. The biogas is often burned to avoid releasing the powerful greenhouse gas methane. Sometimes the heat from burning the biogas is used, for instance, to heat buildings or to power turbines and produce electricity. But heat and electricity are low-value products, so usually the disposal process remains a net economic drain.

In addition to failing to produce a high-value product, anaerobic digestion of sewage and biological wastes is frequently slower and more incomplete than would be desired. Anaerobic microbial digestion also produces hydrogen sulfide and other sulfhydryl compounds that corrode metal pipes and fermentation tanks and cause odors that are objectionable to neighbors of the waste-treatment plant.

New methods of disposing of sewage and other biological or organic wastes are needed. Preferably the methods would allow a more complete and efficient conversion of the wastes. Preferably the methods would remove or convert odor-causing compounds. Preferably the methods would produce a higher value product than current methods.

SUMMARY

The invention provides methods for producing liquid fuel, which may be in specific embodiments higher alcohols (containing 2 or more carbons), in particular ethanol, methanol, or diesel fuel, from biological wastes such as manure, sewage, and crop wastes, as well as from other organic materials. In the methods, organic material is first fermented by anaerobic microorganisms to a biogas consisting primarily of methane and carbon dioxide. The biogas is then converted to synthesis gas consisting primarily of CO and $H_2$.

The synthesis gas (syngas) is then contacted with a catalyst, such as the ruthenium catalyst described in U.S. Pat. No. 4,333,852, that catalyzes the condensation of CO and $H_2$ to form liquid fuel, preferably alcohol and typically mixed alcohols consisting primarily of ethanol. Fuel alcohol is a high value product.

One aspect of the invention involves the use of $CO_2$ reforming in the conversion of biogas to synthesis gas:

$$CH_4+CO_2 \rightarrow 2CO+2H_2 \quad CO_2 \text{ reforming}$$

The $CO_2$ reforming is preferably done in combination with partial oxidation or steam reforming of methane in the biogas.

Methane is typically converted to sythesis gas by partial oxidation or stem reforming:

$$CH_4+\tfrac{1}{2}O_2 \rightarrow CO+2H_2 \quad \text{partial oxidation}$$

$$CH_4+H_2O \rightarrow CO+3H_2 \quad \text{steam reforming}$$

Neither of those two reactions converts $CO_2$ to synthesis gas, and thus the $CO_2$ in biogas would not go to fuel formation. By adding $CO_2$ reforming, some of the $CO_2$ is also converted to CO in synthesis gas and goes toward liquid fuel synthesis.

In addition to increasing the yield of alcohol (or diesel) synthesis from biogas due to allowing $CO_2$ to go into alcohol, $CO_2$ reforming also improves the $H_2$:CO ratio for that purpose. Synthesis of methanol from synthesis gas can operate at an $H_2$:CO ratio of close to 2:

$$CO+2H_2 \rightarrow CH_3OH$$

But synthesis of higher alcohols or alkanes produces water, and water in turn consumes CO and produces $H_2$ in the water-gas shift reaction.

$$2CO+4H_2 \rightarrow C_2H_5OH+H_2O$$

$$CO+H_2O \rightarrow CO_2+H_2 \text{ water-gas shift reaction}$$

The result is that synthesis of ethanol, higher alcohols, and diesel fuels requires more CO and a lower $H_2$:CO ratio. $CO_2$ reforming produces an $H_2$:CO ratio of 1, while partial oxidation produces a ratio of 2 and steam reforming produces a ratio of 3. Including $CO_2$ reforming along with partial oxidation or steam reforming increases the formation of CO and improves the $H_2$:CO ratio for $C_2+$ alcohol synthesis.

The conversion of $CO_2$ to CO in $CO_2$ reforming allows the carbon of $CO_2$ to go into alcohol, and using $CO_2$ reforming in syngas production also improves the $H_2$:CO ratio for $C_2+$ alcohol and alkane production. In both these ways, $CO_2$ reforming improves the yield of alcohol from biogas.

$CO_2$ reforming in one embodiment is combined with partial oxidation. Combining the two can be advantageous because $CO_2$ reforming is an endothermic reaction, and partial oxidation is an exothermic reaction. By combining the two reactions, the $CO_2$ reforming reaction absorbs heat from the partial oxidation reaction, which lessens the problem of dissipating heat from the partial oxidation reaction. The heat from the partial oxidation reaction also helps to drive the $CO_2$ reforming reaction to products.

In contrast, steam reforming and $CO_2$ reforming are both endothermic reactions that are spontaneous only above about 1000 K. Thus, if these two reactions are combined, continuous heat must be applied to the reactions. But combining $CO_2$ reforming and steam reforming is advantageous as well. Stem reforming produces an $H_2$:CO ratio of 3, higher than the ratio of 2 produced by partial oxidation. Thus, when steam reforming is used, there is a greater need to combine $CO_2$ reforming in order to lower the $H_2$:C ratio. Stem reforming also has an advantage over partial oxidation in that partial oxidation requires an input of pure oxygen (air is not usually adequate), and steam reforming avoids the need for expensive pure oxygen.

Thus, the invention provides a method of producing alcohol comprising: (a) fermenting organic material in a fermentation mixture to a biogas comprising methane and $CO_2$; and (b) converting at least a portion of the biogas to synthesis gas comprising CO and $H_2$ by a process comprising: (i) a $CO_2$ reforming reaction of $CH_4+CO_2$ to $2CO+2H_2$; and (ii) a partial oxidation reaction of $CH_4+\tfrac{1}{2}O_2$ to $CO+2H_2$ or a steam reforming reaction of $CH_4+H_2O \rightarrow CO+3H_2$. The method further involves (c) contacting the synthesis gas with a catalyst to produce an alcohol product mixture; and (d) purifying alcohol from the alcohol product mixture, wherein the purified alcohol comprises less than 5% methanol and at least 70% $C_2+$ alcohols by weight. An amount of $CO_2$ equivalent to at least 20% (preferably at least 30%) of the $CO_2$ in the biogas is converted in the $CO_2$ reforming reaction, and at least 20% (preferably at least 30%) of the $CH_4$ in the biogas is converted in the partial oxidation reaction or the steam reforming reaction. Typically the $CO_2$ reformed would be $CO_2$ from the biogas, but it could come from another source. As discussed elsewhere, the $CO_2$ in the biogas can be separated out from the biogas and recycled to the fermentation mixture to promote methane formation, or can be used as a substrate for alcohol synthesis with the alcohol synthesis catalyst. And $CO_2$ can be produced or directed from other points, such as burning unreacted synthesis gas for heat, which produces $CO_2$, and using the combustion exhaust $CO_2$ in the $CO_2$ reforming reaction. Thus, non-biogas $CO_2$ can also be used in the $CO_2$ reforming reaction.

Another embodiment of the invention provides a method of producing liquid fuel comprising: (a) fermenting organic material in a fermentation mixture to a biogas comprising methane and $CO_2$; and (b) converting at least a portion of the biogas to synthesis gas comprising CO and $H_2$ by a process comprising: (i) a $CO_2$ reforming reaction of $CH_4 + CO_2$ to $2CO + 2H_2$; and (ii) a partial oxidation reaction of $CH_4 + \frac{1}{2}O_2$ to $CO + 2H_2$ or a steam reforming reaction of $CH_4 + H_2O \rightarrow CO + 3H_2$. The method further involves (c) contacting the synthesis gas with a catalyst to produce a liquid fuel product mixture comprising alcohol or diesel fuel. An amount of $CO_2$ equal to at least 20% (preferably at least 30%) of the $CO_2$ in the biogas is converted in the $CO_2$ reforming reaction, and at least 20% (preferably at least 30%) of the $CH_4$ in the biogas is converted in the partial oxidation reaction or the steam reforming reaction.

Another embodiment of the invention provides an apparatus for producing $C_2+$ alcohol from organic material, containing: (a) a fermentation vessel containing a fermentation mixture; (a) being functionally coupled to (b) a device for producing synthesis gas comprising CO and $H_2$ from biogas comprising $CO_2$ and $CH_4$, the device comprising comprising (i) a $CO_2$ reforming catalyst for catalyzing $CO_2$ reforming of methane and (ii) a partial oxidation catalyst for catalyzing partial oxidation of methane or a steam reforming catalyst for catalyzing the steam reforming of methane; (b) being functionally coupled to (c) a catalyst for converting synthesis gas to an alcohol mixture containing at least 70% $C_2+$ alcohols by weight.

Another embodiment of the invention provides an apparatus for producing liquid fuel from organic material, comprising: (a) a fermentation vessel containing a fermentation mixture; (a) being functionally coupled to (b) a device for producing synthesis gas comprising CO and $H_2$ from biogas comprising $CO_2$ and $CH_4$, the device comprising (i) a $CO_2$ reforming catalyst for catalyzing $CO_2$ reforming of methane and (ii) a partial oxidation catalyst for catalyzing partial oxidation of methane or a steam reforming catalyst for catalyzing the steam reforming of methane; (b) being functionally coupled to (c) a catalyst for converting synthesis gas to a liquid fuel selected from methanol, $C_2+$ alcohols, and diesel fuel and a combination thereof.

DETAILED DESCRIPTION

Definitions

"Biogas" as used herein refers to a gas produced by the fermentative anaerobic metabolism of microorganisms. The biogases described herein contain methane and typically contain carbon dioxide as their major constituents.

The term "fermenting" organic material as used herein refers to digestion of the organic material by microorganisms using anaerobic respiration.

The term "partially oxidizing" as used herein refers to incomplete oxidation of a reduced substrate by reaction with oxygen or another oxidizing agent. An example is conversion of methane to a more oxidized compound other than carbon dioxide, e.g., methanol or carbon monoxide. In a particular embodiment, partially oxidizing a biogas involves reacting methane with $O_2$ to produce CO and $H_2$. "Partially oxidizing" the biogas includes partially oxidizing all of the biogas and partially oxidizing a portion of the biogas.

The term "sulfhydryls" as used herein refers to SH groups or to compounds having one or more SH groups. The term "sulfhydryls" includes, e.g., hydrogen sulfide, methanethiol, ethanethiol, and 2-mercaptoethanol.

The term "sulfided, nanosized transition metal catalyst" refers to a catalyst composed primarily of a transition metal or a combination of transition metals, where the particles have a mean particle diameter less than 200 nm, preferably less than 100 nm, and where the metal is sulfided.

The term "volatile organic acid" refers to a compound having a COOH group and containing 6 or fewer carbon atoms. It includes formic acid, acetic acid, propionic acid, and butyric acid.

The terms "$C_2+$ alcohols" and "$C_3+$ alcohols" refer to alcohols having, respectively, two or more and three or more carbons.

The terms "alcohol" and "purified alcohol" produced by the methods of the invention include mixtures of alcohols and mixtures containing alcohols and other components, including in some cases water, aldehydes, ketones, ethers, esters, organic acids, and acid anhydrides. Preferably the alcohol and purified alcohol products of the methods of the invention consist of greater than 50%, more preferably greater than 60%, more preferably greater than 70%, more preferably greater than 80%, more preferably greater than 90%, and more preferably still greater than 95% by weight alcohols.

The term "volatile organics" refers to the mass of material in a biomass that is liquid or solid after drying at 105° C. and gasified after heating to 550° C. in air.

DESCRIPTION

The invention provides methods of producing liquid fuel involving the steps of (1) fermenting organic material in a fermentation mixture to a biogas containing methane, (2) converting at least a portion of the biogas to synthesis gas containing CO and $H_2$, and (3) contacting at least a portion of the synthesis gas with a catalyst to produce liquid fuel—$C_2+$ alcohols, methanol, or diesel fuel.

Figure 1:
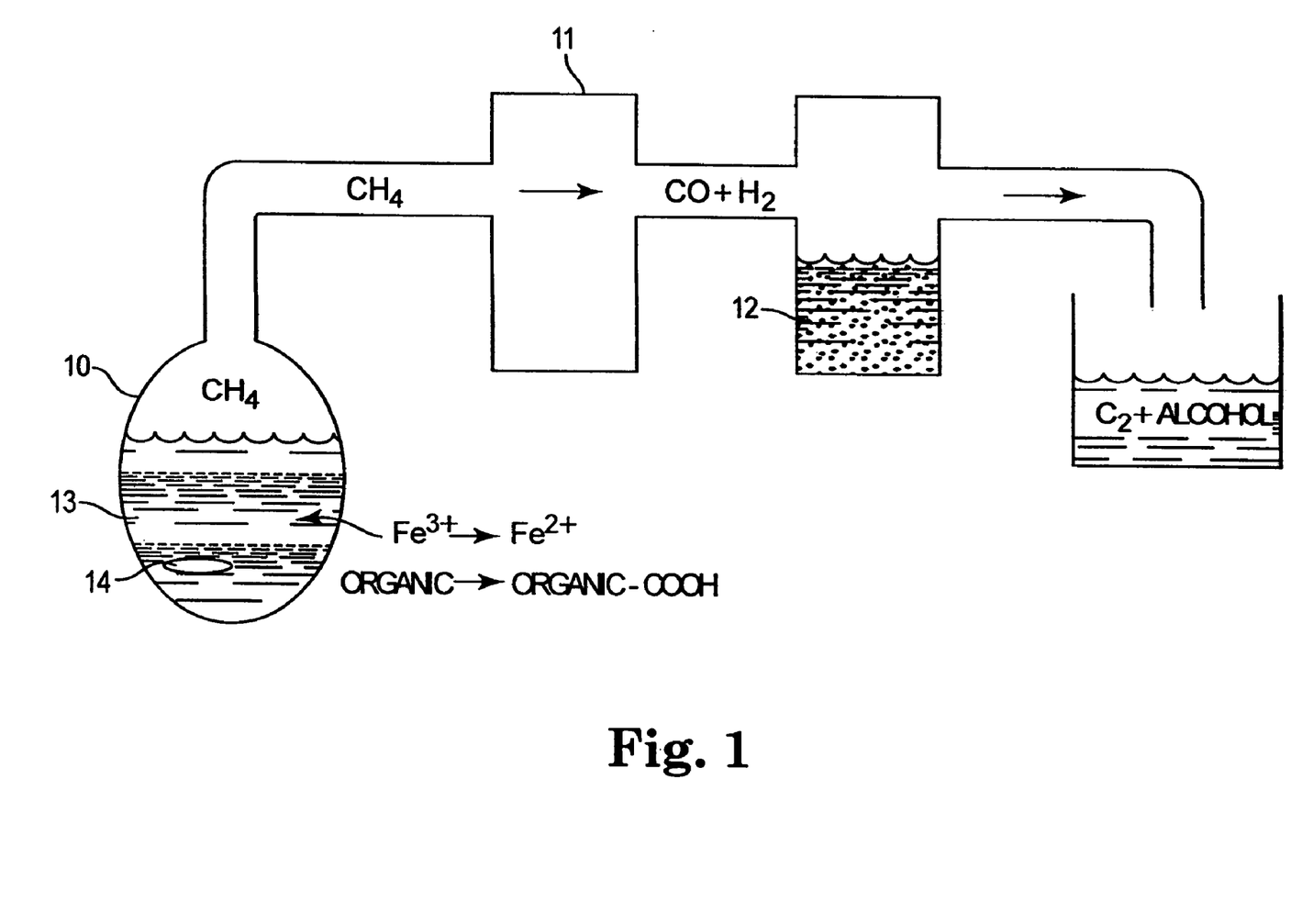
FIG. 1 is a schematic diagram of an apparatus of the invention for producing alcohol from organic material.

FIG. 1 is a schematic drawing of an apparatus of the invention. The apparatus includes a fermentation vessel 10 holding a fermentation mixture 13. The fermentation mixture preferably includes an iron-reducing microorganism 14 that enhances the efficiency of the fermentation. The iron-reducing microorganism 14 reduces $Fe^{3+}$ and produces at least one volatile organic acid (a compound having a COOH group and 6 or fewer carbon atoms) from organic substrates. The fermentation produces a biogas that includes $CH_4$ and occupies the head space of the fermentation vessel. The biogas comprising $CH_4$ passes to a device 11 for producing synthesis gas containing CO and $H_2$. The device 11 can be or include, for instance, a steam reformer, partial oxidation unit, a $CO_2$ reformer, or a combination thereof. Preferably it includes a $CO_2$ reformer in combination with a steam reformer or partial oxidation unit. The synthesis gas passes over and contacts a catalyst 12 to be converted to a $C_2+$ alcohol (e.g., ethanol, propanol, butanol, or a mixture thereof).

In some embodiments of the methods and apparatuses of the invention, the fermentation mixture contains a microorganism that reduces $Fe^{3+}$ and that produces at least one volatile organic acid (typically a mixture of acids containing predominantly acetic acid) from organic substrates. In some embodiments the microorganism produces acetic acid. In some embodiments, the microorganism reduces $Fe^{3+}$ to $Fe^{2+}$. In some embodiments, the microorganism reduces $Fe^{3+}$ to $Fe^{2+}$ and produces acetic acid.

The preferred iron-reducing microorganism is deposited with the American Type Culture Collection under accession number ATCC 55339. Thus, in some embodiments, the microorganism is derived from ATCC 55339. By "derived from ATCC 55339," it is meant that the iron-reducing microorganism grows from the ATCC 55339 culture, is one of the species represented in the culture, or is selected from the culture, e.g., by mutagenesis and selection for an improved strain.

In some embodiments, the microorganism is ATCC 55339.

ATCC 55339 enhances the efficiency of conversion of the organic material to biogas. The conversion efficiency is measured as chemical oxygen demand (COD) destroyed by the fermentation divided by the starting COD of the organic material. This approximates (methane+$CO_2$ produced)/(volatile organics). Volatile organics is defined as the amount of organic material gasified by treatment at 550° C. in air. The inventors have found that fermentation of dairy manure for 12 days at 95° F. using just the native flora found in the manure gives a conversion efficiency of 46-52%. With the addition of ATCC 55339 and magnetite as an iron source, this increases significantly.

ATCC 55339 reduces $Fe^{3+}$ to $Fe^{2+}$ and produces a mixture of volatile acids, including acetic acid, propionic acid, and butyric acid. It can use $Fe^{3+}$ from solution or extract it from an insoluble iron source such as magnetite or taconite.

It is believed that ATCC 55339 enhances the efficiency of fermentation first because it can use a sometimes abundant external electron acceptor, namely $Fe^{3+}$, which enhances the speed and efficiency of breaking down the organic substrates. Second, it is believed to enhance the efficiency of the fermentation because it produces acetic acid and other volatile organic acids, and these are good substrates for the methanogenic archaea (archaebacteria) to convert to $CH_4$ and $CO_2$. Accordingly, while ATCC 55339 is particularly preferred, any microorganism that reduces $Fe^{3+}$ and produces at least one volatile organic acid will enhance the yield of biogas production and therefore the yield of ethanol.

In one embodiment of the invention, the fermentation mixture further contains an iron source. The iron source preferably includes $Fe^{3+}$. In principle, the iron source can be a more reduced form of iron, such as $Fe^0$, and be oxidized in situ to $Fe^{3+}$ by chemical or microbial action. But under anaerobic fermentation conditions, more reduced iron is not expected to be oxidized to $Fe^{3+}$.

Thus, preferably the iron source comprises $Fe^{3+}$. An iron source that comprises $Fe^{3+}$ can involve $Fe^{3+}$ in solution or a complexed insoluble form of iron where some of the iron atoms are in the 3+ oxidation state, e.g., magnetite or taconite. In particular embodiments, the iron source is magnetite. In other particular embodiments, it is taconite.

In some embodiments of the methods of the invention, the method involves partially oxidizing the biogas. This increases the ratio of CO to $H_2$ in the syngas as compared to steam reforming the biogas. Partial oxidation of methane produces a ratio of $2H_2$ per CO. Steam reforming produces a ratio of $3H_2$ per CO. The increased CO to $H_2$ ratio from partial oxidation decreases the amount of methanol and increases the amount of ethanol and higher alcohols produced from the syngas.

Methods of partial oxidation are well known, and units for partial oxidation of methane to CO and $H_2$ are commercially available. For instance, partial oxidation can be accomplished by oxygen-starved burning.

In some embodiments of the invention, a portion of the biogas is partially oxidized and a portion is steam reformed. Steam reforming involves the reaction of methane with water vapor at high temperatures and pressures to produce CO and $H_2$. Steam reformers, like partial oxidation units, are commercially available.

In some embodiments of the invention, the method of producing liquid fuel includes steam reforming a portion or all of the biogas. Steam reforming may be used in combination with partial oxidation and/or more preferably $CO_2$ reforming.

The liquid fuel produced in the process can be methanol, $C_2+$ alcohols, or diesel, or a combination of two or more of these.

Fuel alcohol preferably is predominantly higher alcohols. Alcohol mixtures that are too rich in methanol are sensitive to phase separation in the presence of water, which is ubiquitous in gasoline systems. Thus, preferably the alcohol products are rich in $C_2+$ alcohols and have low methanol content. In some embodiments the alcohol comprises less than 5% methanol by weight. Preferably the alcohol comprises at least 70% by weight $C_2+$ alcohols. In some embodiments, the alcohol comprises less than 0.5% by weight methanol. In some embodiments, the alcohol comprises at least 60% by weight ethanol. In some embodiments the alcohol comprises less than 0.5% by weight methanol and at least 60% by weight ethanol. In some embodiments, the alcohol comprises at least 92.1% by weight ethanol. In some embodiments, the alcohol comprises at least 5% or at least 10% by weight $C_3+$ alcohols.

Several factors can contribute to obtaining alcohol with a high $C_2+$ alcohol content. One is use of a syngas having a higher ratio of CO to $H_2$ (lower ratio of $H_2$:CO). As discussed above, partial oxidation of methane produces a higher CO:$H_2$ ratio than steam reforming. Another factor involved in obtaining alcohol with a high $C_2+$ alcohol content is using a catalyst and reaction conditions that promote $C_2+$ alcohol formation over methanol formation. Suitable catalysts include the catalysts described in Bao, J. et al., 2003, *Chem. Commun.* 2003: 746-747; U.S. Pat. No. 4,235,801; and U.S. Pat. No. 4,333,852. The catalyst described in Bao et al. is a K—Co—Mo/C catalyst. It is formed by the following procedure. $Co(NO_3)_2$ and $(NH_4)_6Mo_7O_{24}$ aqueous solutions are prepared and mixed at a Co/Mo molar ratio of 0.5. Citric acid is added to the solution under constant stirring (citric acid/metalic ions molar ratio=0.1). Then a $K_2CO_3$ solution is dripped slowly into the solution (K/Mo molar ratio=0.1). The pH value of the solution is adjusted to 3.5 with HCOOH and $NH_4OH$. The solution is kept in a water bath at 65° C. until the solution becomes a gel. The gel is dried at 120° C. for 15 hours and calcined in argon at 400° C. for 4 hours. Suitable reaction conditions with the synthesis gas are a temperature of 230° C., a pressure of 6.0 MPa, and a gas hour space velocity of 9600 hours$^{-1}$. Under these conditions, the CO conversion was 7.5%, the alcohol selectivity was 60.4% of carbon, the alcohol space-time yield was 296 g per kg-hour, and the $C_2+$ alcohol to methanol ratio was 1.48. (Bao, J. et al., 2003, *Chem. Commun.* 2003:746-747.)

Other suitable catalysts are described in U.S. Pat. No. 4,333,852. The catalysts are ruthenium catalysts with a halogen promoter and a phosphine oxide compound as a solvent. An example of catalyst preparation and alcohol synthesis involves the following procedure. 16 milligrams of Ru atoms as triruthenium dodecacarbonyl, 5.6 mmoles of elemental iodine, and 75 ml of tripropylphosphine oxide are placed in a back-mixed autoclave with a net volume of 128 ml and heated with stirring to 55° C. The reactor is pressurized to 500 psi with CO, heated to 240° C., and then pressurized with a $H_2$/CO mixture ($H_2$/CO ratio=2.0) to 6,000 psi. As the reaction proceeds the pressure drops. When it drops to 500 psi, the reactor is repressurized with the synthesis gas to 6,000 psi. With this procedure, ethanol is produced at a rate of 2.05 moles/liter/hour at a selectivity of 50 weight percent. The ethanol plus methanol selectivity is 74 weight percent.

Perhaps the most important mechanism to obtain alcohol with low methanol content and high $C_2+$ alcohol content is to fractionate the alcohol as it is formed into a $C_2+$-rich alcohol fraction and a methanol-rich fraction, harvest the $C_2+$-rich alcohol fraction, and recirculate the methanol-rich fraction into the synthesis gas for contact with the catalyst. Adding methanol to the synthesis gas reaction on the catalyst forces the equilibrium of the $CO+2H_2 \rightarrow CH_3OH$ reaction to the left (Gavin, D. G. and Richard D. G., European Patent Application 0 253 540). With the equilibrium preventing further net formation of methanol, the CO and $H_2$ react to form ethanol and other $C_2+$ products. Recirculated methanol can also be a reactant for formation of $C_2+$ products by reaction with CO, $H_2$, and/or a second molecule of methanol. If all methanol produced is recirculated, there is no net production of methanol.

In the methanol-recirculation process, the alcohol products from the alcohol catalyst or catalysts are fractionated into a $C_2+$-rich alcohol fraction and a methanol-rich fraction. This is preferably done by condensing the $C_2+$ alcohols from the product mixture at a temperature and pressure below the boiling point of the $C_2+$ alcohols and above the boiling point of methanol. The gaseous methanol-rich fraction is then mixed with the synthesis gas for contact with the catalyst.

The alcohols produced in the methods of the invention, including the $C_2+$-rich alcohol fraction separated from the methanol-rich fraction, can be further processed or fractionated. For instance, ethanol can be separated from other alcohols and other components in the mixtures. The mixtures often contain propanol, butanol, and isobutanol, which can be purified. Acetaldehyde, acetic acid, acetic anhydride, and other components may be present in the alcohol mixtures and can be purified or separated from the alcohols.

In some embodiments of the invention, the fermenting involves fermenting for at least 12 hours at a temperature in the range of 45-100° C., followed by fermenting for at least 12 hours at a temperature in the range of 0-44° C. ATCC 55339 is only active at mesophilic temperatures, so if ATCC 55339 is used in the fermentation, it must be used in the fermentation step at a temperature in the range of 0-44° C.

In some embodiments of the invention, the step of contacting the synthesis gas with the catalyst produces heat that is used to heat the fermentation mixture or to heat the steam reforming or $CO_2$ reforming reaction.

In some embodiments of the invention, the iron-reducing microorganism produces $Fe^{2+}$ that binds sulfhydryls in the fermentation mixture and/or in the biogas.

In some embodiments, the step of fermenting organic material to a biogas involves the steps of feeding the organic material into a vessel, fermenting and mixing the organic material in anaerobic conditions in the vessel to form the biogas, discontinuing the mixing to allow particulate unfermented organic material to settle in the vessel resulting in the formation of a low-suspended-solid supernatant, decanting the supernatant from the vessel, and repeating at least the feeding and fermenting steps. This method improves the efficiency of gasification of the organic material, as compared to a two-vessel system (U.S. Pat. No. 5,185,079). In the two-vessel system, fermentation occurs in one vessel and then the wastewater flows to a separate solids separation unit where settling takes place. The settled solids are then recycled to the fermentation vessel (U.S. Pat. No. 5,185,079). The one-vessel system also requires less capital investment.

In one embodiment of the one-vessel method, the method further involves withdrawing at least a portion of the biogas from the vessel, optionally with the use of a vacuum, immediately before the settling step.

In some embodiments of the methods of the invention, the organic material comprises dairy manure. In other embodiments, the organic material comprises hog manure, turkey manure, chicken manure, slaughterhouse waste, municipal sewage, or crop waste. One crop waste suitable for fermenting in the methods of the invention is sugar beet waste (e.g., sugar beet tailings).

In some embodiments, the organic material comprises forest products waste (e.g., sawdust).

In some embodiments of the invention, the fermenting involves fermenting at a temperature in the range of 0-44° C. (with mesophilic organisms). In some embodiments, the fermenting involves fermenting at a temperature in the range of 45-100° C. (with thermophilic organisms).

In some embodiments of the invention, the catalyst is a sulfided, nanosized transition metal catalyst selected from Group VI metals. In some embodiments, the catalyst is a sulfided, nanosized molybdenum catalyst. (U.S. Pat. No. 6,248,796.)

In some embodiments, the sulfided, nanosized transition metal catalyst is suspended in a solvent, e.g., heavy machine oil, and the synthesis gas is contacted with the catalyst at a temperature in the range of 250-325° C. and at a pressure in the range of 500 to 3000 psi.

The catalyst can also be other metal or inorganic catalysts, such as are disclosed in U.S. Pat. Nos. 4,675,344; 4,749,724; 4,752,622; 4,752,623; and 4,762,858.

Preferably, the catalyst is sulfur-free, because a sulfur-containing catalyst leaches sulfur into the alcohol mixtures it produces. Sulfhydryls are undesirable in fuel alcohol because they carry an odor, upon burning they produce sulfur oxides that cause acid rain and human health problems, and they can damage engine parts in internal combustion engines. Thus, preferably the alcohols contain less than 10 ppm sulfur atoms, more preferably less than 1 ppm sulfur atoms. This can be achieved by removing sulfhydryls from biogas before the biogas is converted to synthesis gas, and then using a sulfur-free catalyst for conversion of synthesis gas to alcohol. One method to remove sulfhydryls from biogas is to contact the biogas with a metal cation that binds sulfhydryls, such as $Fe^{2+}$. Another method is to contact the biogas with another type of agent that binds sulfhydryls, such as amine compounds, which may be immobilized on a resin.

Alternatively, sulfhydryls can be removed from the alcohol product. One method to do this is to contact the alcohol with a metal cation that binds sulfhydryls, such as $Fe^{2+}$. Another method is to contact the alcohol with another type of agent that binds sulfhydryls, such as amine compounds, which may be immobilized on a resin.

In particular embodiments of the methods and products of the invention, the alcohol or purified alcohol has less than 10 ppm or less than 1 ppm (by weight) sulfur atoms in sulfhydryl compounds. In other embodiments, the alcohol or purified alcohol has less than 10 ppm or less than 1 ppm sulfur atoms (in any form).

The methods of the invention can also involve contacting the biogas with a sulfur scrubber separate from the $Fe^{2+}$ produced by the iron-reducing organism. The sulfur scrubber may remove one or more of sulfhydryls, $H_2S$, anionic oxidized forms of sulfur (e.g., sulfate and sulfite), and COS.

Sulfhydryls and other forms of sulfur can also be removed from the alcohol after it is formed. Thus, one embodiment of the invention provides a method of producing alcohol involving (a) fermenting organic material in a fermentation mixture to a biogas comprising methane; (b) converting at least a portion of the biogas to synthesis gas comprising CO and $H_2$; (c) contacting at least a portion of the synthesis gas with a catalyst to produce alcohol; (d) contacting the alcohol with a scrubber to remove sulfhydryls from the alcohol; and (e) purifying the alcohol, wherein the purified alcohol contains less than 10 ppm sulfur atoms, less than 5% methanol, and at least 70% $C_2+$ alcohols by weight.

In principle, the catalyst for converting syngas to alcohol could be a biological catalyst, such as a microorganism or purified enzyme that converts CO and $H_2$ to ethanol or other alcohols. Some of these are described in Bredwell, M. D., et al., 1999, *Biotechnol. Prog.* 15:834-844; Vega, J. L., et al., 1989, *Appl. Biochem. and Biotech.* 20/21:781; Barik, S. et al., 1988, *Appl. Biochem. and Biotech.* 18:379.

In some embodiments of the methods of the invention, the alcohol includes $C_2+$ alcohols and the yield of $C_2+$ alcohols is at least 4 gallons, at least 5 gallons, or at least 6 gallons per 1000 cubic feet of methane in the biogas.

In particular embodiments of the methods, the conversion of volatile organics in the fermentation mixture to biogas is at least 50%, at least 65%, at least 70%, or at least 75% efficient.

In some embodiment of the methods, the alcohol includes $C_2+$ alcohols and the yield of $C_2+$ alcohols is at least 6 gallons per 1000 cubic feet of methane in the biogas, and the conversion of volatile organics in the fermentation mixture to biogas is at least 65% efficient.

In some embodiments of the invention, the organic material fermented includes cellulose, and the method includes digesting the organic material with cellulase before or during the fermentation step. The cellulase can be an isolated enzyme or cellulase in a cellulase-containing microorganism.

One embodiment of the invention provides a method of producing alcohol comprising: (1) fermenting organic material in a fermentation mixture to a biogas comprising methane, (2) removing odiferous compounds from the biogas by contacting the biogas with a metal cation that binds sulfhydryls, (3) converting at least a portion of the biogas to synthesis gas comprising CO and $H_2$, and (4) contacting at least a portion of the synthesis gas with a catalyst to produce alcohol.

The metal cation that binds sulfhydryls can be $Fe^{2+}$. In some embodiments, the $Fe^{2+}$ is formed by microbial action from iron in other oxidation states. In some embodiments, the microbial action involves reducing $Fe^{3+}$ to $Fe^{2+}$ by an iron-reducing microorganism that produces at least one volatile organic acid from organic substrates.

In other embodiments, the metal cation that binds sulfhydryls is a cation of zinc or copper.

In some embodiments of the methods of the invention, an exogenous microorganism (i.e., an organism in addition to the organisms found in the organic material to be fermented) is added to the fermentation mixture to enhance the efficiency or speed of biogas production.

The alcohols produced by the methods of the invention have an advantage over grain-fermented ethanol as a fuel additive in that the present alcohols include substantial amounts of propanol, n-butanol, iso-butanol, and pentanol. These $C_3+$ alcohols boost the octane of fuel more effectively than ethanol. Thus, in some embodiments of the alcohols produced by processes of the invention, the alcohols include at least 5% or at least 10% $C_3+$ alcohols by weight.

In some embodiments of the apparatuses of the invention, the apparatus includes a purification unit functionally coupled to the catalyst for converting synthesis gas to alcohol. The purification unit may be for instance a condenser to preferentially condense at least one $C_2+$ alcohol from the alcohol mixture, generating a $C_2+$-rich alcohol fraction and a methanol-rich fraction. In another embodiment, the purification unit is a condenser to condense methanol, $C_2+$ alcohols, and water together as a liquid fraction, coupled to a distillation unit to then separate the liquid fraction into a water-enriched fraction, a methanol-enriched fraction, and a $C_2+$ alcohol-enriched fraction. In another embodiment, the purification unit includes a liquid or gas chromatography separator unit.

In some embodiments, in addition to the purification unit, the apparatus includes a recirculation unit functionally coupled to the catalyst and the purification unit. The recirculation unit recirculates at least a portion of the methanol-rich fraction produced by the purification unit to the catalyst for reaction with synthesis gas.

Where the apparatus is used to produce primarily methanol or diesel, instead of $C_2+$ alcohol, the purification unit may be designed to separate purify methanol or diesel, e.g., from water and other components in the liquid fuel product mixture.

Another aspect of the invention involves a method of producing alcohol comprising: (a) fermenting organic material in a fermentation mixture to a biogas comprising methane and $CO_2$; and (b) converting at least a portion of the biogas to synthesis gas comprising CO and $H_2$ by a process comprising: (i) a $CO_2$ reforming reaction of $CH_4+CO_2$ to $2CO+2H_2$; and (ii) a partial oxidation reaction of $CH_4+\frac{1}{2}O_2$ to $CO+2H_2$, or a steam reforming reaction of $CH_4+H_2O$ to $CO+3H_2$. The method further involves (c) contacting the synthesis gas with a catalyst to produce an alcohol product mixture; and (d) purifying alcohol from the alcohol product mixture, wherein the purified alcohol comprises less than 5% methanol and at least 70% $C_2+$ alcohols by weight. At least 30% of the $CO_2$ in the biogas is converted in the $CO_2$ reforming reaction, and at least 30% of the $CH_4$ in the biogas is converted in the partial oxidation reaction or the steam reforming reaction.

In one embodiment, the method further involves before step (b) removing sulfhydyls from the biogas. This can be done by adding a source of $Fe^{3+}$ to the fermentation mixture where the fermentation mixture contains a microorganism that reduces $Fe^{3+}$ and produces at least one volatile organic acid. Where the microorganism reduces $Fe^{3+}$ to $Fe^{2+}$, the $Fe^{2+}$ binds sulfhydyls and removes them from the biogas. Preferably the microorganism is ATCC 55339 or is derived from ATCC 55339.

Sulfhydyls can also be removed from the biogas by a scrubber. The scrubber may be, for instance amino groups immobilized on a resin. This can be in addition to or as alternative to including an iron-reducing microorganism and a source of $Fe^{3+}$ in the fermentation mixture.

In some embodiments, water is removed from the biogas before step (b). This reduces the amount of steam reforming of the methane. Steam reforming can be undesirable because it produces too high a ratio of $H_2$:CO, a ratio of 3:1. Furthermore, if water is not consumed in the steam reforming reaction, it is passed on in the synthesis gas to the alcohol synthesis catalyst or catalysts. In the alcohol synthesis reaction from syngas, water is undesirable because it consumes CO in the water-gas shift reaction, discussed above in the summary. It also is a product of ethanol and higher alcohol synthesis, so its addition will tend to drive the equilibrium away from ethanol and higher alcohol synthesis.

But in other embodiments, steam reforming is used instead of partial oxidation to convert methane to synthesis gas. Steam reforming can be desirable because it avoids the need for a purified oxygen input.

In some embodiments, at least 10%, at least 20%, at least 30%, or at least 50% of the $CO_2$ in the biogas is not converted in step (b) to CO and is present in the synthesis gas contacted with the catalyst in step (c) to make alcohol. In these embodiments, at least a portion of the $CO_2$ in the synthesis gas reacts with $H_2$ in step (c) to produce alcohol. The portion of $CO_2$ in the synthesis gas reacting with $H_2$ in step (c) to produce alcohol in particular embodiments is at least 10%, at least 20%, at least 30%, or at least 50%.

Consuming $CO_2$ in the alcohol production step occurs by the reactions $$CO_2+3H_2 \rightarrow CH_3OH+H_2O$$

$$CH_3OH+CO+2H_2 \rightarrow CH_3CH_2OH+H_2O$$

or $2CO_2+6H_2 \rightarrow CH_3CH_2OH+3H_2O$

These reactions consume hydrogen while consuming less or no CO. So they contribute to a more balanced and efficient consumption of CO and $H_2$ in alcohol production if syngas production is predominantly by partial oxidation, which gives an $H_2$ to CO ratio of close to 2, or steam reforming, which gives an $H_2$ to CO of close to 3. Reducing $CO_2$ in the alcohol production step also results in the carbon from $CO_2$ going to alcohol, which consumes a greenhouse gas and increases alcohol production.

Carbon dioxide also can be recycled to the biodigester to stimulate methane production in the biodigester.

Organisms that produce methane are called methanogens. Methanogens can produce methane from acetate by the reaction acetate+$H_2O\rightarrow$methane+$HCO_3^-$. In what is probably a more important reaction though, methanogens can also produce methane from hydrogen and $CO_2$ by the reaction $4H_2+HCO_3^-+H^+\rightarrow CH_4+3H_2O$. The hydrogen for methanogenesis from carbon dioxide in nature comes from fermentation of reduced carbon substrates. Hydrogen gas can also be supplied directly to a fermenter for methane production.

Thus, in addition to being a fermentation product, $CO_2$ is a crucial electron acceptor for methane production from hydrogen. Anaerobic fermentation generally and methane production specifically are slowed when the carbon dioxide concentration is too low. Carbon dioxide is often a limiting factor in anaerobic methanogenesis. Since $CO_2$ is often a limiting factor, recycling a portion of $CO_2$ (either from the biogas or from the output of the alcohol production reaction) to the fermentation mixture enhances methane production.

Thus, in one embodiment, the method of producing alcohol involves separating at least a portion of the $CO_2$ in the biogas before the step of converting at least a portion of the biogas to synthesis gas and recycling the $CO_2$ into the fermentation mixture to stimulate methane production in the fermentation mixture.

The liquid fuel product mixture typically includes unreacted synthesis gas, water, and in some cases unreacted $CO_2$. The liquid fuel product mixture can be fractionated into a liquid fuel-enriched fraction and a syngas-enriched fraction. The syngas-enriched fraction may in some cases include $CO_2$. In other cases, the liquid fuel product mixture is separated into a liquid fuel-enriched fraction, a syngas-enriched fraction, and a $CO_2$-enriched fraction.

The syngas-enriched fraction and the $CO_2$-enriched fraction can be recycled and reused. In some embodiments, the syngas-enriched fraction is recycled to the liquid fuel synthesis catalyst.

In some embodiments, at least a portion of the syngas-enriched fraction from the liquid fuel product mixture output is burned to produce heat and $CO_2$. The heat can be used at several points in the process, including to heat the fermentation mixture, to heat the biogas in the $CO_2$ reformer, or to heat the biogas in the steam reformer. The $CO_2$ from combustion of the syngas can also be used at several points in the process. It can be recycled to the fermentation mixture, to the liquid fuel catalyst, or to the $CO_2$ reformer. $O_2$ in the $CO_2$-rich combustion exhaust gas should be removed before the $CO_2$ is added to the fermentation mixture, the $CO_2$ reformer, or the liquid fuel catalyst. It can be removed by physico-chemical methods, such as pressure swing adsorption, or by passing the gas through a fermentation mixture containing aerobic and facultative aerobic microorganisms and a reduced carbon substrate for the microorganisms, so that the microorganisms can consume substantially all the oxygen by aerobic respiration.

Where a $CO_2$-enriched fraction is fractionated from the liquid fuel product mixture, the $CO_2$-enriched fraction can be recycled to one or more of the fermentation mixture, the $CO_2$ reforming reaction, or the liquid fuel synthesis catalyst.

In another embodiment, the method of producing alcohol involves fractionating the alcohol product mixture into a purified alcohol fraction, a water-enriched fraction, a synthesis gas-enriched fraction, and a $CO_2$-enriched fraction; wherein at least a portion of the $CO_2$-enriched fraction is recycled to the fermentation mixture.

In another embodiment, $H_2$ is added to the fermentation mixture to stimulate methane production. This may be done without recycling of $CO_2$ or more preferably with recycling of $CO_2$ into the fermentation mixture.

Any $H_2$ added is preferably produced by renewable means, e.g., by water electrolysis where the electricity for electrolysis is produced by solar energy or wind energy. Adding $H_2$ to the fermentation mixture is a way of ultimately converting $H_2$ to a liquid fuel—alcohol or diesel—by the present process. Adding $H_2$ stimulates methane production in the fermentation mixture and goes toward converting $CO_2$ to methane. This increases alcohol or diesel yield from the biogas.

The $CO_2$ reforming reaction and steam reforming reaction are both endothermic reactions that are spontaneous in the forward direction only at high temperatures. They thus need an input of heat. Partial oxidation is an exothermic reaction, and it can provide some or all of the heat needed to drive the $CO_2$ reforming and/or steam reforming reactions where a partial oxidation reaction is used to produce syngas. Where additional heat is needed, or where the partial oxidation reaction is not used, some portion of the biogas can be burned to produce heat to drive the $CO_2$ reforming and/or steam reforming reactions.

In one embodiment, the step of contacting the synthesis gas with a catalyst to produce an alcohol product mixture comprises contacting the synthesis gas with a first catalyst 12a to form methanol, followed by contacting the methanol and unreacted synthesis gas with a second catalyst 12b (FIG. 2) to form $C_2+$ alcohols. The unreacted synthesis gas may be synthesis gas that contacted the first catalyst without reacting, or it may be a portion of the synthesis gas that bypasses the first catalyst to be taken directly to the second catalyst for reaction with methanol.

Suitable first catalysts for methanol synthesis are the MK-101 and MK-121 catalysts from Haldor Topsoe (Houston, Tex. and Lyngby, Denmark). These are sulfur-free catalysts.

Suitable second catalysts for ethanol and higher alcohol synthesis include the catalysts described in Bao, J. et al., 2003, *Chem. Commun.* 2003:746-747; U.S. Pat. No. 4,235, 801; and U.S. Pat. No. 4,333,852. These are also sulfur-free catalysts.

In particular embodiments, the first and second catalysts are both sulfur-free.

Figure 3:
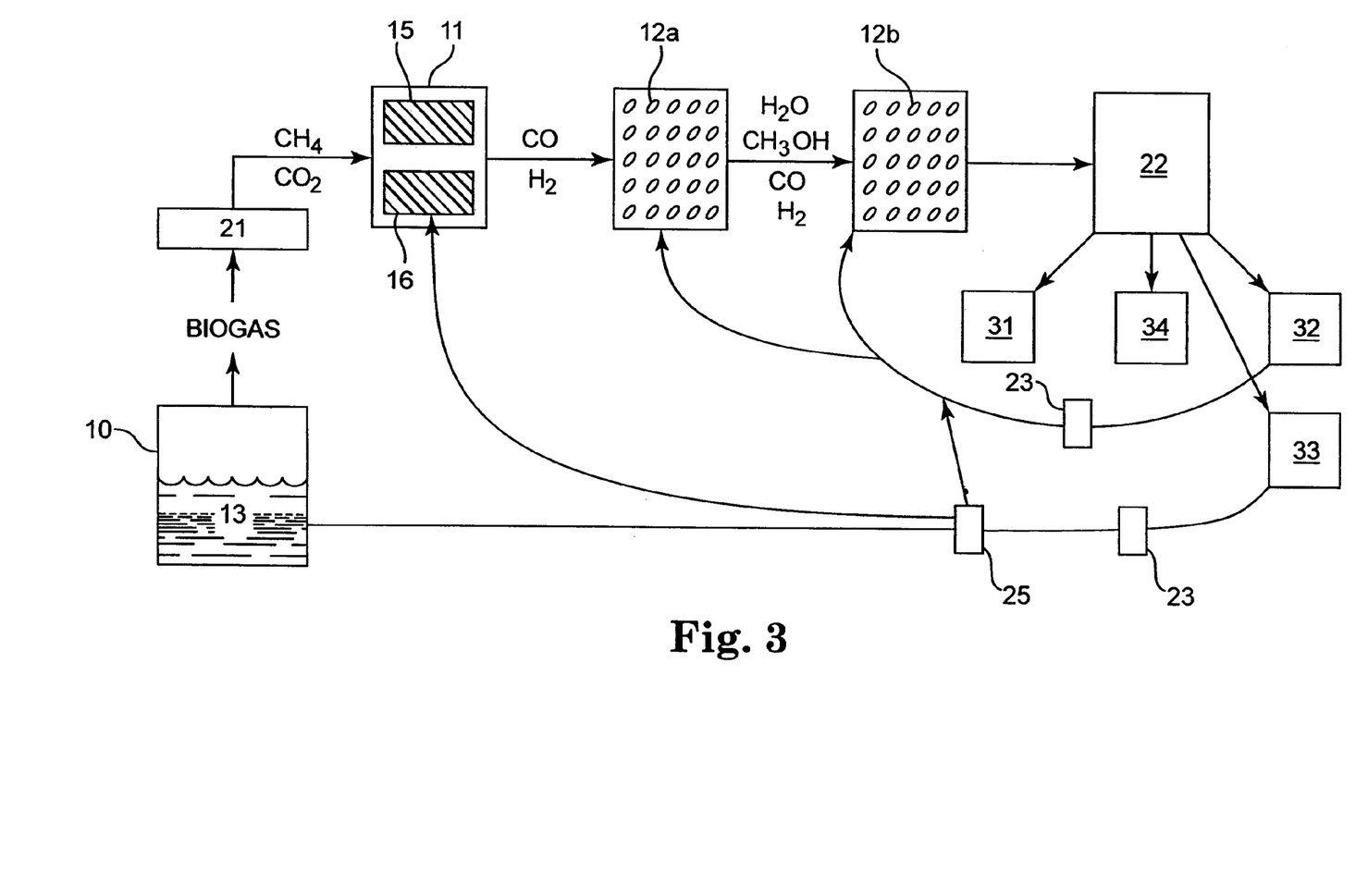
FIG. 3 is a schematic diagram of an apparatus of the invention for producing alcohol that includes a fractionator for fractionating output from the alcohol synthesis catalyst and includes recirculation of $CO_2$ and synthesis gas from the alcohol synthesis catalyst.

In particular embodiments, the step of purifying alcohol from the alcohol product mixture comprises fractionating the alcohol product mixture into a purified alcohol fraction, a $CO_2$-enriched fraction, and a synthesis gas-enriched fraction. Preferably fractionation of the alcohol product mixture also produces a water-enriched fraction, but water may alternatively be exclusively in one or more of the other fractions. This may be done with fractionator 22 as shown in FIG. 3. Fractionation can be done, for instance, by condensing alcohols and water to liquid, and separating $CO_2$ from $H_2$ and CO in the gas fraction with a pressure swing adsorption unit to generate a $CO_2$-enriched fraction and a synthesis gas-enriched fraction.

The synthesis gas-enriched fraction from fractionator 22 is preferably recycled to the alcohol production catalyst or catalysts.

The $CO_2$-enriched fraction is preferably recycled to one or more of (I) the fermentation mixture, (II) the $CO_2$-reforming catalyst, and (III) the alcohol production catalyst or catalysts.

As discussed above, in one embodiment, the method of producing alcohol involves separating at least a portion of the $CO_2$ in the biogas before the step of converting at least a portion of the biogas to synthesis gas. The separated portion of the $CO_2$ from the biogas can be mixed with the $CO_2$-enriched fraction from fractionator 22 to be recycled to one or more of (I) the fermentation mixture, (II) the $CO_2$-reforming catalyst, and (III) the alcohol production catalyst or catalysts.

Where the alcohol production catalyst includes a methanol production catalyst 12a and a higher alcohol production catalyst 12b, the synthesis gas-enriched fraction and/or the $CO_2$-enriched fraction may be recycled to one or both of the catalysts 12a and 12b. In one embodiment, they are recycled to methanol production catalyst 12a and not directly to catalyst 12b.

In the methods of the invention, it is possible to catalyze both (i) the $CO_2$ reforming reaction and (ii) the partial oxidation reaction and/or the steam reforming reaction with a single catalyst, or to perform the reactions without a catalyst. But preferably, the partial oxidation reaction is catalyzed by a partial oxidation catalyst. Preferably the $CO_2$ reforming reaction is catalyzed by a $CO_2$ reforming catalyst distinct from the partial oxidation catalyst. Preferably, the steam reforming reaction, if used, is catalyzed by a catalyst distinct from the partial oxidation catalyst, if a partial oxidation reaction is used. The steam reforming catalyst may or may not be distinct from the $CO_2$ reforming catalyst.

In preferred embodiments of the methods, the yield of $C_2+$ alcohols is at least 6 gallons per 1000 cubic feet of methane in the biogas, and the conversion of volatile organics in the fermentation mixture to biogas is at least 65% efficient. Use of an iron-reducing microorganism, preferably with supplementation with a source of $Fe^{3+}$, helps to increase the conversion of volatile organics in the fermentation mixture to biogas to at least 65% efficiency. Recycling $CO_2$ to the fermentation mixture also helps to increase the efficiency of conversion of volatile organics to biogas.

The steps discussed herein also increase the yield of $C_2+$ alcohols. These include using $CO_2$ reforming along with partial oxidation to form synthesis gas. Reducing biogas $CO_2$ to methanol and higher alcohols with $H_2$ from the syngas also helps increase the $C_2+$ alcohol yield. Recycling a $CO_2$-enriched fraction from the alcohol product mixture to the $CO_2$ reforming reaction and/or the alcohol production reaction also increases the $C_2+$ alcohol yield. Recycling a syngas-enriched fraction to the alcohol production catalyst also helps to increase the alcohol yield.

The $CO_2$ recycled from the mixed alcohol product may be metered to be allocated for recycling in the optimal proportions between the $CO_2$ reforming reaction, the alcohol synthesis reaction, and the fermentation mixture.

As discussed above, preferably the alcohol production catalyst or catalysts are sulfur-free, and the alcohol comprises less than 10 ppm sulfur atoms. In particular embodiments, the alcohol comprises less than 1 ppm sulfur atoms.

Figure 2:
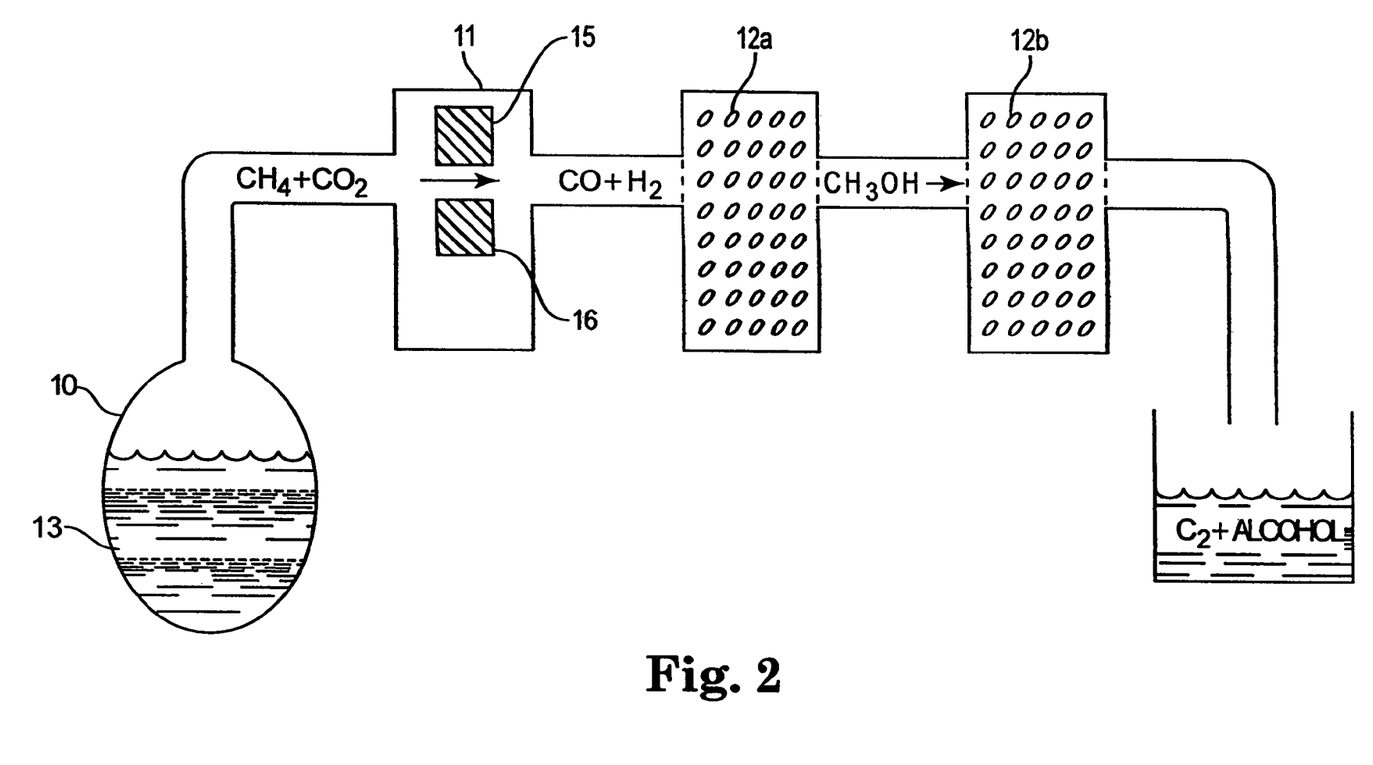
FIG. 2 is a schematic diagram of an apparatus of the invention for producing alcohol that includes a partial oxidation catalyst and a $CO_2$ reforming catalyst for producing synthesis gas from biogas.

One embodiment of an apparatus of the invention is shown in FIG. 2. FIG. 2 shows an apparatus for producing $C_2+$ alcohol from organic material. It includes a fermentation vessel 10 holding a fermentation mixture 13. The fermentation vessel 10 is functionally coupled to a device 11 for producing synthesis gas comprising CO and $H_2$. The device 11 includes a partial oxidation catalyst or steam reforming catalyst 15 for catalyzing the partial oxidation or steam reforming of methane and a $CO_2$ reforming catalyst 16 for catalyzing the $CO_2$ reforming of methane. The device 11 is functionally coupled to a catalyst 12 for converting synthesis gas to an alcohol mixture containing at least 70% $C_2+$ alcohols by weight. In FIG. 2 a particular embodiment is shown where the catalyst 12 includes a first catalyst 12a for converting synthesis gas to methanol and a second catalyst 12b for converting methanol and synthesis gas to an alcohol mixture comprising at least 70% $C_2+$ alcohols by weight.

FIG. 3 shows an embodiment of the alcohol production apparatus that further includes a fractionator 22 functionally coupled to catalyst 12 to fractionate output from the catalyst 12 into an alcohol-enriched fraction 31, a synthesis gas-enriched fraction 32, and a $CO_2$-enriched fraction 33. FIG. 3 also shows a water-enriched fraction 34. The fractionator 22 is functionally coupled to a pump or pumps 23 that pumps the synthesis gas-enriched fraction 32 to alcohol synthesis catalysts 12a and/or 12b and the $CO_2$-enriched fraction 33 to device 11 to contact the $CO_2$ reforming catalyst 16 and to alcohol synthesis catalyst 12. Part of the $CO_2$-enriched fraction 33 may also be pumped to the fermentation mixture 13 in fermentation vessel 10 to serve as a substrate for methane production.

Where catalyst 12 includes separate catalysts 12a and 12b for methanol and $C_2+$ alcohol synthesis respectively, the synthesis gas-enriched fraction 32 and $CO_2$-enriched fraction 33 may be pumped to one or both of catalysts 12a and 12b.

FIG. 3 also shows a sulfyhdryl scrubber 21 functionally coupled to the fermentation vessel 10 to remove sulfhydryls from the biogas.

FIG. 3 also shows a meter 25 that divides $CO_2$-enriched fraction 33 into specified portions for recycling to one or more of fermentation mixture 13, $CO_2$-reforming catalyst 16, and alcohol synthesis catalyst 12. The meter 25 preferably not only divides flow from $CO_2$-enriched fraction 33 into portions destined for 13, 16, and 12, but records the absolute volume or percent of the flow going to each destination.

Figure 4:
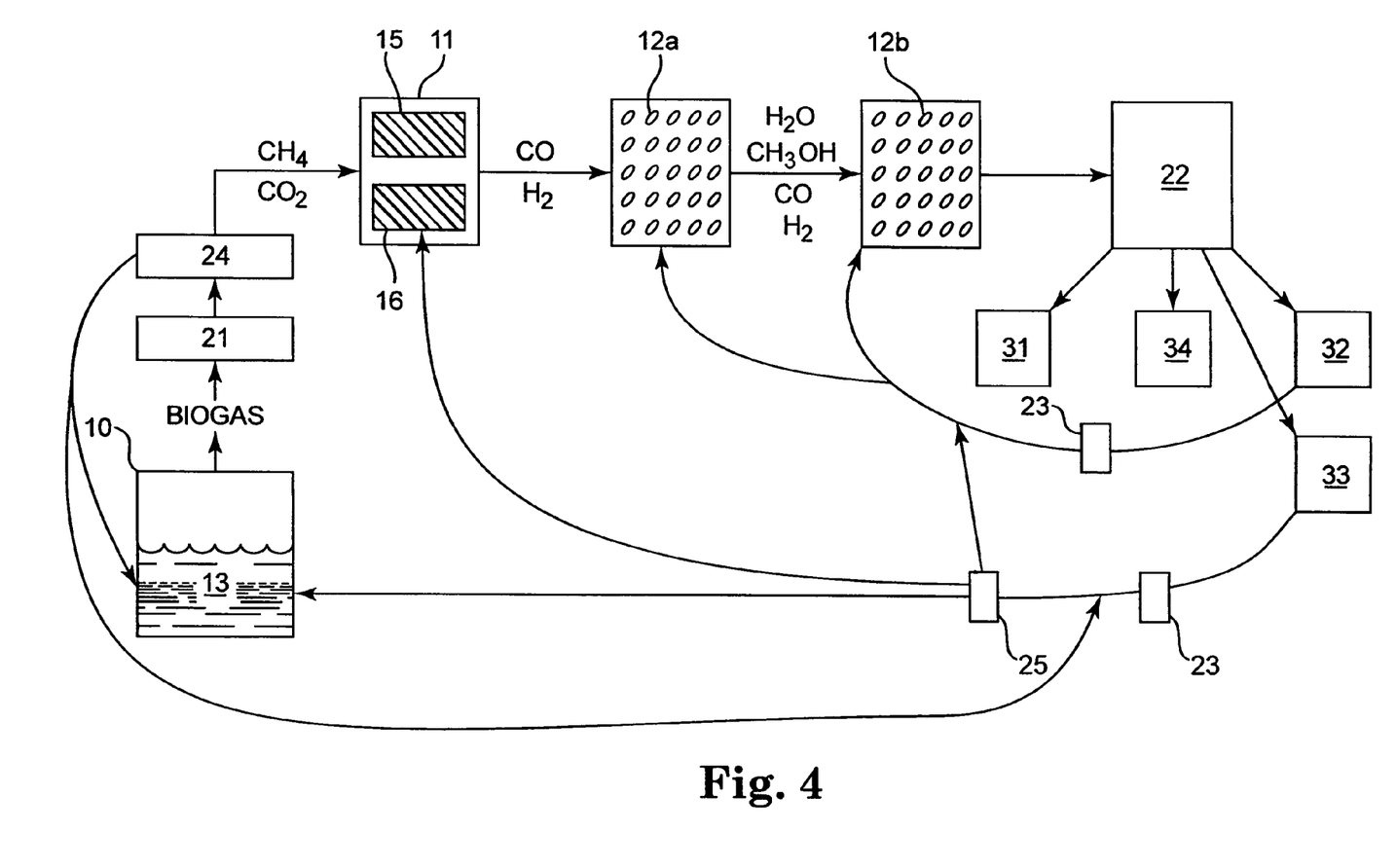
FIG. 4 is a schematic diagram of an apparatus of the invention for producing alcohol that includes recirculation of $CO_2$ into the fermentation mixture.

FIG. 4 shows another embodiment of the apparatus that includes a $CO_2$ fractionator 24 that removes all or a portion of the $CO_2$ from the biogas. The removed $CO_2$ may optionally be recycled into the fermentation mixture 13 in fermentation vessel 10 to serve as a substrate for methane production in the fermentation mixture and increase methane production (see U.S. patent application Ser. No. 11/821,935, titled "Bio-Recycling of Carbon Dioxide Emitted from Power Plants"). It can also or instead be directed to merge with flow from $CO_2$-enriched fraction 33 to be distributed between fermentation mixture 13, $CO_2$-reforming catalyst 16, and alcohol synthesis catalyst 12. A portion of the $CO_2$ may also be disposed of, e.g., vented to the atmosphere.

Figure 5:
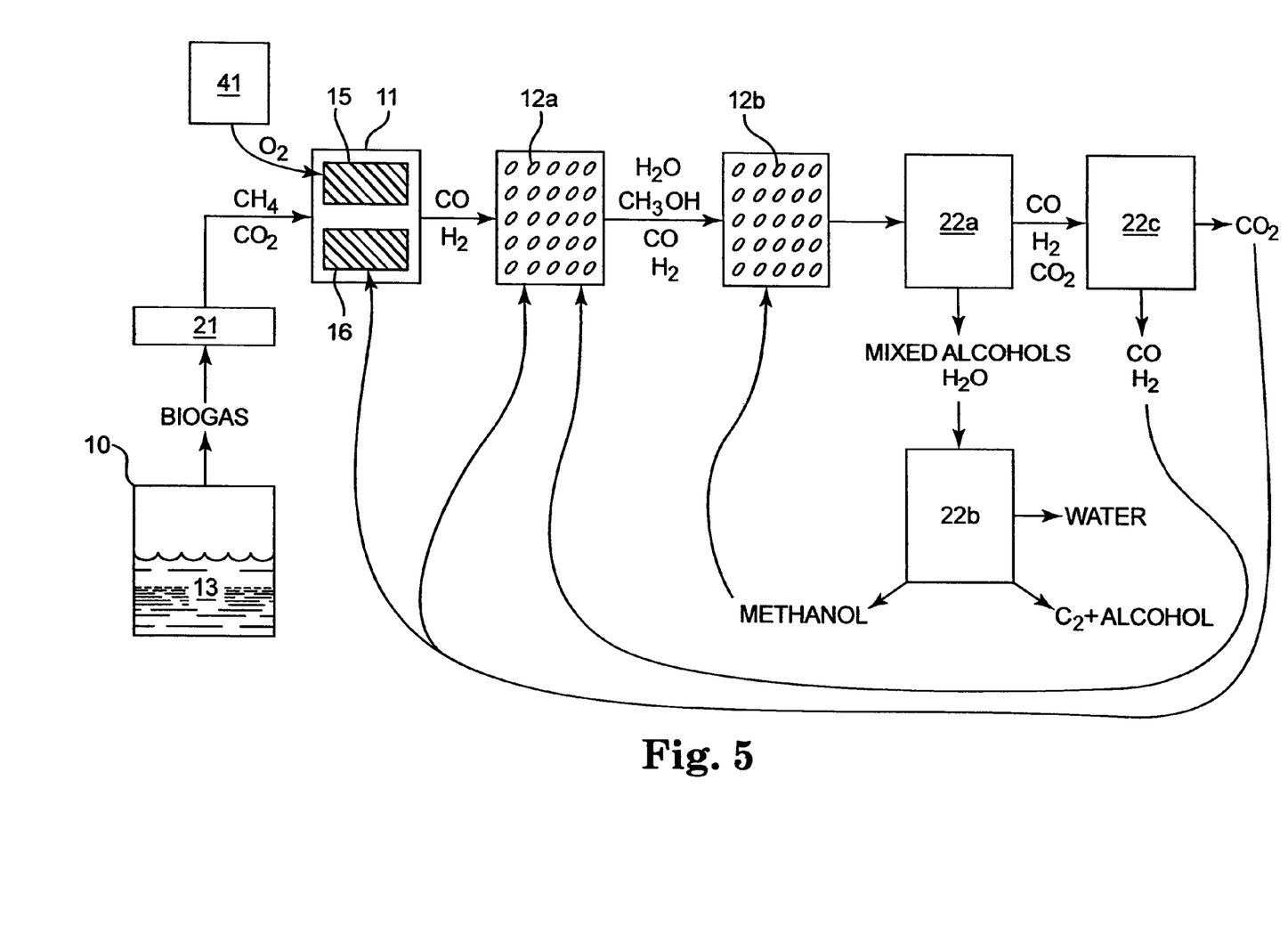
FIG. 5 is a schematic diagram of an example of an apparatus of the invention for producing alcohol.

The fractionator 22 may consist of (i) a condensor 22a that condenses a liquid fraction containing water and alcohols from a gas fraction containing CO, $H_2$, and $CO_2$; (ii) an alcohol separation unit 22b that separates the liquid fraction into methanol, $C_2+$ alcohols, and water, and (iii) a $CO_2$ scrubber 22c that separates the gas fraction into a $CO_2$-enriched fraction 33 and a synthesis gas-enriched fraction 32, as shown in FIG. 5. The alcohol separation unit 22b may operate by, for instance, distillation or chromatographic separation.

Some embodiments of the methods of the invention for producing a liquid fuel mixture, the liquid fuel is or comprises methanol. In a specific embodiment, the method involves purifying methanol from the liquid fuel product mixture wherein the purified methanol comprises at least 90% methanol by weight. Preferably in this embodiment, methanol is at least 50%, more preferably at least 90%, by weight of reduced carbon compounds in the liquid fuel mixture.

In other embodiments, the liquid fuel is or comprises diesel fuel. In some embodiments, the method comprises purifying diesel fuel from the liquid fuel product mixture, wherein at least 90% by weight of reduced carbon compounds in the purified diesel boil between 150° C. and 350° C.

In specific embodiments, at least 50% by weight of reduced carbon compounds in the liquid fuel product mixture boil between 150° C. and 350° C.

Purifying diesel fuel from the liquid fuel product mixture can comprise fractionating the liquid fuel product mixture into a purified diesel fraction, a water-enriched fraction, a synthesis gas-enriched fraction optionally containing $CO_2$, and optionally a separate $CO_2$-enriched fraction; wherein the synthesis gas-enriched fraction is recycled to the liquid fuel-production catalyst and the $CO_2$-enriched fraction, if present, is recycled to one or more of the fermentation mixture, the $CO_2$ reforming reaction, and the liquid fuel-production catalyst.

One embodiment of the invention provides an apparatus for producing $C_2+$ alcohol from organic material, comprising: (a) a fermentation vessel containing a fermentation mixture; (a) being functionally coupled to (b) a device for producing synthesis gas comprising CO and $H_2$ from biogas comprising $CO_2$ and $CH_4$, the device comprising (i) a $CO_2$ reforming catalyst for catalyzing $CO_2$ reforming of methane and (ii) a partial oxidation catalyst for catalyzing partial oxidation of methane or a steam reforming catalyst for catalyzing the steam reforming of methane; (b) being functionally coupled to (c) a catalyst for converting synthesis gas to a liquid fuel selected from methanol, $C_2+$ alcohols (e.g., an alcohol mixture containing at least 70% $C_2+$ alcohols by weight), and diesel fuel, and a combination thereof.

In specific embodiments, the apparatus includes (d) a fractionator functionally coupled to the catalyst (c) to fractionate output from the catalyst (c) into a liquid fuel fraction (e.g., an alcohol-enriched fraction), a synthesis-gas fraction, and a $CO_2$-enriched fraction; (d) being functionally coupled to (e) a pump or pumps functionally linked to (b) and (c) that pumps the synthesis gas-enriched fraction to catalyst (c) and the $CO_2$-enriched fraction to device (b) to contact the $CO_2$ reforming catalyst and/or to catalyst (c).

In specific embodiments, the pump or pumps of (e) pump the $CO_2$-enriched fraction to at least two of (I) the $CO_2$ reforming catalyst, (II) the liquid fuel synthesis catalyst (c), and (III) fermentation vessel (a); the apparatus further comprising a meter to distribute specified portions of the $CO_2$-enriched fraction to at least two of (I) the $CO_2$ reforming catalyst, (II) liquid fuel synthesis catalyst (c), and (III) fermentation vessel (a).

The invention will now be illustrated with the following non-limiting examples.

EXAMPLES

Comparative Example 1

Dairy manure, including some water used to wash manure from where it was collected, was placed in a stainless steel or Plexiglas fermentation reactor as described in U.S. Pat. No. 5,185,079. The reactors were purchased from Columbia Tech Tank (Kansas City, Mo.). The manure was first fermented in a thermophilic digester at 135° F. No additional microbes were added. The fermentation relied on the flora found in the manure. The reactor was mixed for 2 minutes each hour. At the end of every 8 hours period, the fermentation mixture was mixed, 1/30 of the volume was withdrawn and transferred to a second vessel for mesophilic fermentation, and an equal volume of manure was added to the thermophilic digester. Thus, the average residence time in the thermophilic digester was 10 days.

A second fermenter vessel housed a mesophilic fermentation. The mesophilic fermentation occurred at 95° F. Again no microbes were added, and the fermentation depended on the native flora found in the manure. Both the mesophilic and the thermophilic digesters were approximately ¾ filled with liquid, with ¼ of the volume of the vessel being gas head space. The mesophilic fermenter followed an 8-hour cycle time, with (a) 6 hours of reacting, where the mixture was mixed for 2 minutes each hour; (b) 1.5 hours without mixing to allow the solids to settle; (c) 15 minutes decanting "gray water" liquid supernatant equal to 1/54 of the reactor liquid volume; (d) 15 minutes to add a volume from the thermophilic digester equal to the volume of gray water withdrawn. With 1/54 of the volume replaced every 8 hours, the mesophilic reactor had an average residence time of 18 days.

The settled sludge can be periodically removed from the mesophilic reactor, dried, and sold as fertilizer.

Biogas was withdrawn from the head space of both the thermophilic and mesophilic fermenters continuously.

The biogas from the two fermenters was collected. It contained approximately 69-75% methane, and 25-29% carbon dioxide, with the remainder including small amounts of nitrogen and hydrogen sulfide.

The biogas was partially oxidized using an oxygen-starved gas burner to convert the methane to synthesis gas containing primarily CO and $H_2$ in a 1:2 ratio. The carbon dioxide in the biogas is unaffected by the partial oxidation and is present also in the synthesis gas.

To demonstrate the feasibility of alcohol synthesis, a separately obtained synthesis gas sample containing 18% $H_2$, 28% CO, 30% $CO_2$, 15% $CH_4$ and 9% $N_2$ was contacted with a nanosized sulfided molybdenum catalyst suspended in heavy machine oil, as described in U.S. Pat. No. 6,248,796, at 200-325° C. and 500-3000 psi. The catalyst produced an alcohol mixture that contained 232 g/l methanol, 126 g/l ethanol, 168 g/l propanol, and 69 g/l butanol and higher alcohols, and approximately 120 g/l water (due to the high $CO_2$ content).

Waste heat from the catalyst was transferred to heat the fermenters, using an ethylene glycol heat transfer medium.

Methane production can be calculated by multiplying the conversion factor 8 cubic feet methane per pound volatile organics, times the volatile organics conversion efficiency. The conversion efficiency of volatile organics in the substrate for the fermentation mixture to biogas was 45-55%, as calculated by the loss of volatile liquid and solid organics. Approximately 6-7 gallons of alcohol mixture was produced per 1000 cubic feet of methane.

All of the methods described herein can also be adapted to produce diesel fuel instead of $C_2+$ alcohols. The second catalyst 12b can be a catalyst to produce primarily saturated long chain alkanes.

Example 1

This example used a single fermenter vessel, which housed a mesophilic fermentation at 95° F. Dairy manure was added to the fermenter as in Comparative Example 1. ATCC 55339 was added to the fermenter at the initiation of fermentation. No other microorganisms were added. The fermenter followed an 8-hour cycle time, with (a) 6 hours of reacting, where the mixture was mixed for 2 minutes each hour; (b) 1.5 hours without mixing to allow the solids to settle; (c) 15 minutes decanting "gray water" liquid supernatant equal to 1/36 of the reactor liquid volume; (d) 15 minutes to add a volume from the thermophilic digester equal to the volume of gray water withdrawn. With 1/36 of the volume replaced every 8 hours, the mesophilic reactor had an average residence time of 12 days. Granulated iron oxide (magnetite) was added to the bioreactor by automatic augur or similar device. Approximately 1/8 of a pound magnetite was added per day per cow.

Despite just a 12-day residence and the lack of a thermophilic digestion, with the iron-reducing bacterium ATCC 55339 added, the volatile organics conversion efficiency was 75-86%. This compares to about 50-65% in comparable conditions without the bacteria.

The biogas was converted to syngas, and the syngas converted to alcohol as in Comparative Example 1.

The gray water removed from the reactor in Example 1 contains phosphate and polymers containing phosphate formed from the manure. Phosphates lead to eutrophication of ground waters, and so should be minimized in discharged wastewaters. However, the gray water also contains $Fe^{2+}$ formed by the iron-reducing microbe. If the gray water is aerated after removal from the fermenter, the ferrous iron is oxidized to ferric, which binds and precipitates the phosphates. The precipitate can be separated out before discharge of the gray water, and can be dried and sold as a phosphate- and iron-rich fertilizer. See U.S. Pat. Nos. 5,667,673; 5,543,049; and 5,620,893.

Example 2

Waste water from a yeast manufacturing facility (growing yeast on sugar beet waste) is digested in an anaerobic fermenter as described in Example 1 to generate biogas. Biogas containing 600 scf/hour of methane is produced. An oxygen stream of 300 scf/hour is mixed with the biogas stream, and the gases enter a partial oxidation reactor for reaction at 850° C. at ambient pressure in the presence of a commercial catalyst to form synthesis gas consisting primarily of $H_2$ and CO.

The synthesis gas exits the partial oxidation system and is cooled and compressed.

Synthesis gas is contacted with the ruthenium catalyst whose preparation is described above and in U.S. Pat. No. 4,333,852 at 6,000 psi and 240° C. to produce a product mixture containing ethanol as the most abundant product, substantial methanol, and higher alcohols.

After exiting the reactor, the gas stream is de-pressurized, cooled, and the ethanol and higher ($C_3+$) alcohols condensed and removed. This ethanol-rich alcohol fraction is routed to a storage drum.

Unreacted synthesis gas and reaction by-products (methanol, carbon dioxide, and water) exit the condenser and are scrubbed with $H_2O$ and $CO_2$ scrubbers to remove $H_2O$ and $CO_2$.

Unreacted synthesis gas and methanol are reheated, re-pressurized, and mixed with incoming synthesis gas from the partial oxidation unit. The gas mixture is then recirculated through the alcohol reactor.

Example 3

Referring to FIG. 5, fermentation mixture 13 is placed in fermentation vessel 10. The fermentation mixture includes magnetite as a source of $Fe^{3+}$ and ATCC 55339 as a microorganism that reduces $Fe^{3+}$ to $Fe^{2+}$ and produces organic acids. The feedstock for the fermenter can be, for instance, dairy manure, raw sewage, or sugar beet pulp. The fermenter produces biogas containing $CO_2$ and $CH_4$, which is scrubbed with a sulfyhdryl scrubber 21 to remove sulfhydyls to below 10 ppm sulfur atoms, preferably below 1 ppm. The biogas then is passed to device 11 for converting the biogas to syngas. This includes partial oxidation unit 15 and $CO_2$ reforming unit 16. Catalysts for partial oxidation and $CO_2$ reforming are available from Oxford Catalysts Group, PLC (Oxford, United Kingdom) prepared according to U.S. published patent applications US20050250863 and US20040242941. These are sulfur-free molybdenum carbide catalysts. An oxygen generator 41 produces $O_2$ and feeds it to the partial oxidation catalyst 15. The oxygen generator 41 can be a pressure swing adsorption unit, for instance. The partial oxidation and $CO_2$ reforming reactions are conducted by isothermal operation at 1560° F. and 150 psig.

The device 11 produces syngas containing CO and $H_2$, which are passed to methanol catalyst 12a. The syngas is compressed prior to contacting catalyst 12a to 1000 psig. The methanol reaction is conducted at 570° F. Methanol catalyst 12a is preferably MK-101 or MK-121 from Haldor Topsoe (Houston, Tex. and Lyngby, Denmark). The output of methanol catalyst 12a is methanol, $H_2O$, and unreacted CO and $H_2$. These are passed to higher alcohol catalyst 12b. The higher alcohol catalyst can be the sulfur-free catalysts described in Bao, J. et al., 2003, *Chem. Commun.* 2003:746-747; U.S. Pat. No. 4,235,801; or U.S. Pat. No. 4,333,852. The higher alcohol reaction is conducted at 625° F., 950 psig.

The output from higher alcohol catalyst 12b includes mixed higher alcohols, methanol, water, $CO_2$, CO and $H_2$. The output is passed to condensor 22a, which condenses alcohols and water, separating them from CO, $H_2$, and $CO_2$. The mixed alcohols and water pass to alcohol distillation unit 22b, which separates them into a methanol fraction, and $C_2$+ alcohol fraction, and a water fraction. The methanol is recirculated to higher alcohol catalyst 12b to be converted to $C_2$+ alcohols. The CO, $H_2$, and $CO_2$ from the condensor 22a are passsed to $CO_2$ scrubber 22c to separate out the $CO_2$ from the CO and $H_2$. The $CO_2$ is then recirculated to $CO_2$ reforming catalyst 16 to be used in the $CO_2$ reforming reaction and to methanol catalyst 12a. The CO and $H_2$ are recirculated to methanol catalyst 12a to be converted to methanol.

Collectively, condensor 22a, alcohol distillation unit 22b, and $CO_2$ scrubber 22c are an example of a fractionator 22 in FIG. 3.

Example 4

Figure 6:
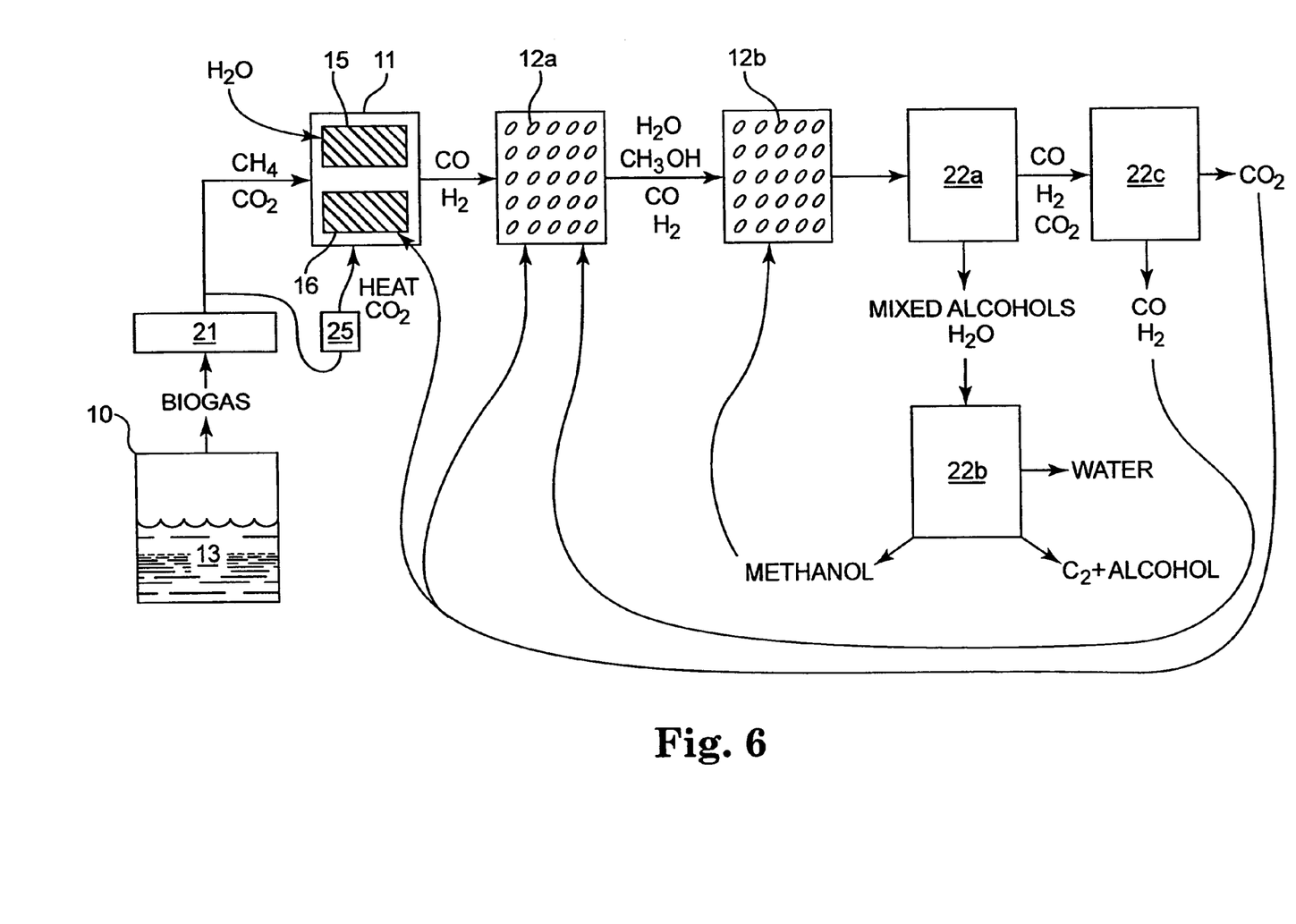
FIG. 6 is a schematic diagram of an example of another apparatus of the invention for producing alcohol.

Referring to FIG. 6, fermentation mixture 13 is placed in fermentation vessel 10. The fermenter produces biogas containing $CH_4$ and $CO_2$, which is scrubbed with a sulfhydryl scrubber 21 to remove sulfhydryls and reduce the sulfhydryl concentration in the biogas to below 10 ppm sulfur atoms, preferably below 1 ppm.

A portion of the biogas output from scrubber 21 is directed to burner 25 for burning. Burning the biogas produces heat and $CO_2$. The apparatus includes a syngas-production device 11 for converting biogas to synthesis gas. The syngas-production device 11 includes steam reformer 15 and $CO_2$ reformer 16. Along with biogas, steam is directed to steam reformer 15 as a substrate for the reaction. The heat output from 25 that arises from burning a portion of the biogas is used to heat steam reformer 15 and $CO_2$ reformer 16 in device 11. The $CO_2$ output from burning a portion of the biogas in burner 25 may also be used as feedstock for the $CO_2$ reformer 16. The $CO_2$ output from burning a portion of the biogas may also or alternatively be fed to the fermentation mixture 13 in fermenter 10 (see U.S. patent application Ser. No. 11/821,935, titled "Bio-Recycling of Carbon Dioxide Emitted from Power Plants"). The $CO_2$ from combustion of the biogas may also or alternatively be fed to an alcohol formation catalyst or specifically the methanol catalyst 12a. In any of these destinations, the $CO_2$ is preferably free of $O_2$. To remove $O_2$ from the stream, any technique known in the art can be used including pressure swing adsorption. A preferred technique to remove $O_2$ is to pass the $CO_2$-rich exhaust gas through a fermenter containing aerobic and facultative anaerobic organisms and a reduced organic substrate to consume the $O_2$ in the exhaust stream by microbial action.

Alternatively the $CO_2$-containing exhaust from burning the portion of the biogas in burner 25 may be vented to the atmosphere.

The portion of the biogas that is burned to heat the reformers in syngas-production device 11 may be directed to the burner 25 after scrubbing for sulfhydryls in scrubber 21 or without passing through scrubber 21. In FIG. 6 the portion of the biogas going to burner 25 is shown first passing through scrubber 21. That is suitable if the $CO_2$ from combustion of the biogas is fed into the $CO_2$ reformer. If the exhaust from combustion of the biogas is just vented it may not be necessary to first scrub the biogas for sulfhydyls.

The remainder of the biogas leaving the sulfhydryl scrubber 21 goes directly to device 11 for producing syngas without passing through burner 25. The majority of the biogas takes this route directly to syngas-producing device 11.

The device 11 produces syngas containing CO and $H_2$, which are passed to methanol catalyst 12a. The syngas is compressed prior to contacting catalyst 12a to 1000 psig. The methanol reaction is conducted at 570° F. Methanol catalyst 12a is preferably MK-101 or MK-121 from Haldor Topsoe (Houston, Tex. and Lyngby, Denmark). The output of methanol catalyst 12a is methanol, $H_2O$, and unreacted CO and $H_2$. These are passed to higher alcohol catalyst 12b. The higher alcohol catalyst can be the sulfur-free catalysts described in Bao, J. et al., 2003, *Chem. Commun.* 2003:746-747; U.S. Pat. No. 4,235,801; or U.S. Pat. No. 4,333,852. The higher alcohol reaction is conducted at 625° F., 950 psig.

The output from higher alcohol catalyst 12b includes mixed higher alcohols, methanol, water, $CO_2$, CO and $H_2$. The output is passed to condensor 22a, which condenses alcohols and water, separating them from CO, $H_2$, and $CO_2$. The mixed alcohols and water pass to alcohol distillation unit 22b, which separates them into a methanol fraction, and $C_2$+ alcohol fraction, and a water fraction. The methanol is recirculated to higher alcohol catalyst 12b to be converted to $C_2$+ alcohols. The CO, $H_2$, and $CO_2$ from the condensor 22a are passsed to $CO_2$ scrubber 22c to separate out the $CO_2$ from the CO and $H_2$. The $CO_2$ is then recirculated to $CO_2$ reforming catalyst 16 to be used in the $CO_2$ reforming reaction and to methanol catalyst 12a. The CO and $H_2$ are recirculated to methanol catalyst 12a to be converted to methanol.

Collectively, condensor 22a, alcohol distillation unit 22b, and $CO_2$ scrubber 22c are an example of a fractionator 22 in FIG. 3.

All references, patents, and patent documents cited are hereby incorporated by reference.

What is claimed is:

1. A method of producing liquid fuel comprising:
   (a) fermenting organic material in a fermentation mixture to a biogas comprising methane and $CO_2$;
   (b) converting at least a portion of the biogas to synthesis gas comprising CO and $H_2$ by a process comprising:
      (i) a $CO_2$ reforming reaction of $CH_4 + CO_2$ to $2CO + 2H_2$; and
      (ii) a partial oxidation reaction of $CH_4 + \frac{1}{2} O_2$ to $CO + 2H_2$ or a steam reforming reaction of $CH_4 + H_2O$ to $CO + 3H_2$; and
   (c) contacting the synthesis gas with a catalyst to produce a liquid fuel product mixture comprising alcohol or diesel fuel;
   wherein an amount of $CO_2$ equal to at least 30% of the $CO_2$ in the biogas is converted in the $CO_2$ reforming reaction, and at least 30% of the $CH_4$ in the biogas is converted in the partial oxidation reaction or steam reforming reaction.

2. The method of claim 1 wherein the liquid fuel product mixture comprises methanol, the method further comprising:
   (d) purifying methanol from the liquid fuel product mixture wherein the purified methanol comprises at least 90% methanol by weight.

3. The method of claim 1 wherein the liquid fuel product mixture comprises diesel, the method further comprising:
   (d) purifying diesel fuel from the liquid fuel product mixture, wherein at least 90% by weight of reduced carbon compounds in the purified diesel boil between 150° C. and 350° C.

4. The method of claim 3 wherein at least 50% by weight of reduced carbon compounds in the liquid fuel product mixture boil between 150° C. and 350° C.

5. The method of claim 3 wherein step (d) comprises fractionating the liquid fuel product mixture into a purified diesel fraction, a water-enriched fraction, a synthesis gas-enriched fraction, and a separate $CO_2$-enriched fraction; wherein the synthesis gas-enriched fraction is recycled to the catalyst of step (c) and the $CO_2$-enriched fraction is recycled to one or more of the fermentation mixture of step (a), the $CO_2$ reforming reaction of step (b), and the catalyst of step (c).

6. The method of claim 3 wherein step (d) comprises fractionating the liquid fuel product mixture into a purified diesel fraction, a water-enriched fraction, and a synthesis gas-enriched fraction, wherein at least a portion of the synthesis gas-enriched fraction is burned to produce heat and $CO_2$, and the heat is used to heat (i) the fermentation mixture, or (ii) the biogas in the $CO_2$ reforming reaction, or (iii) the biogas in the steam reforming reaction if step (b)(ii) comprises a steam reforming reaction.

7. A method of producing alcohol comprising:
(a) fermenting organic material in a fermentation mixture to a biogas comprising methane and $CO_2$;
(b) converting at least a portion of the biogas to synthesis gas comprising CO and $H_2$ by a process comprising:
(i) a $CO_2$ reforming reaction of $CH_4+CO_2$ to $2CO+2H_2$; and
(ii) a partial oxidation reaction of $CH_4+\frac{1}{2}O_2$ to $CO+2H_2$ or a steam reforming reaction of $CH_4+H_2O$ to $CO+3H_2$;
(c) contacting the synthesis gas with a catalyst to produce an alcohol product mixture; and
(d) purifying alcohol from the alcohol product mixture, wherein the purified alcohol comprises less than 5% methanol and at least 70% $C_2+$ alcohols by weight;
wherein an amount of $CO_2$ equal to at least 30% of the $CO_2$ in the biogas is converted in the $CO_2$ reforming reaction, and at least 30% of the $CH_4$ in the biogas is converted in the partial oxidation reaction or steam reforming reaction.

8. The method of claim 7 wherein reaction (ii) is a partial oxidation reaction.

9. The method of claim 7 wherein reaction (ii) is a steam reforming reaction.

10. The method of claim 7 further comprising before step (b) removing sulfhydryls from the biogas.

11. The method of claim 7 wherein at least 10% of $CO_2$ in the biogas is not converted in step (b) to CO and is present in the synthesis gas contacted with the catalyst in step (c), wherein at least 10% of the $CO_2$ in the synthesis gas reacts with $H_2$ in step (c) to produce alcohol.

12. The method of claim 7 further comprising:
separating at least a portion of the $CO_2$ in the biogas from the biogas before step (b) and recycling the separated portion of $CO_2$ into the fermentation mixture to stimulate methane production in the fermentation mixture.

13. The method of claim 7 wherein step (c) comprises contacting the synthesis gas with a first catalyst to form methanol, followed by contacting the methanol and unreacted synthesis gas with a second catalyst to form $C_2+$ alcohols.

14. The method of claim 7 wherein step (d) comprises fractionating the alcohol product mixture into a purified alcohol fraction, a water-enriched fraction, a synthesis gas-enriched fraction, and a separate $CO_2$-enriched fraction; wherein the synthesis gas-enriched fraction is recycled to the catalyst of step (c) and the $CO_2$-enriched fraction is recycled to one or more of the fermentation mixture of step (a), and the $CO_2$ reforming reaction of step (b).

15. The method of claim 7 wherein step (d) comprises fractionating the alcohol product mixture into a purified alcohol fraction, a water-enriched fraction, and a synthesis gas-enriched fraction, wherein at least a portion of the synthesis gas-enriched fraction is burned to produce heat and $CO_2$, and the heat is used to heat (i) the fermentation mixture, or (ii) the biogas in the $CO_2$ reforming reaction, or (iii) the biogas in the steam reforming reaction if step (b)(ii) comprises a steam reforming reaction.

16. The method of claim 15 wherein at least a portion of the $CO_2$ produced from burning the synthesis gas is recycled to one or more of the fermentation mixture of step (a), the $CO_2$ reforming reaction of step (b), and the catalyst of step (c).

17. The method of claim 14 wherein fractionating the alcohol product mixture into a purified alcohol fraction comprises fractionating the alcohol product mixture into an ethanol fraction and a $C_3+$ alcohol fraction.

18. The method of claim 8 wherein the partial oxidation reaction is catalyzed by a partial oxidation catalyst.

19. The method of claim 18 wherein the $CO_2$ reforming reaction is catalyzed by a $CO_2$ reforming catalyst distinct from the partial oxidation catalyst.

20. The method of claim 9 wherein the $CO_2$ reforming reaction is catalyzed by a $CO_2$ reforming catalyst and the steam reforming reaction is catalyzed by a steam reforming catalyst distinct from the $CO_2$ reforming catalyst.

21. The method of claim 7 wherein the yield of $C_2+$ alcohols is at least 6 gallons per 1000 cubic feet of methane in the biogas.

22. The method of claim 21 wherein the conversion of volatile organics in the fermentation mixture to biogas is at least 65% efficient.

23. The method of claim 7 wherein the catalyst is sulfur-free and the alcohol comprises less than 10 ppm sulfur atoms.

24. The method of claim 23 wherein the alcohol comprises less than 1 ppm sulfur atoms.

* * * * *